an12) United States Patent
Wang et al.

(10) Patent No.: US 10,563,064 B2
(45) Date of Patent: Feb. 18, 2020

(54) ANTHRACENE-BASED ORGANIC DYES AND PREPARATION METHODS THEREOF

(71) Applicant: CHANGCHUN INSTITUTE OF APPLIED CHEMISTRY CHINESE ACADEMY OF SCIENCES, Changchun, Jilin (CN)

(72) Inventors: Peng Wang, Changchun (CN); Yameng Ren, Changchun (CN); Min Zhang, Changchun (CN); Junting Wang, Changchun (CN); Yang Li, Changchun (CN)

(73) Assignee: Changchun Institute of Applied Chemistry Chinese Academy of Sciences, Changchun, Jilin (CN)

( * ) Notice: Subject to any disclaimer, the term of this patent is extended or adjusted under 35 U.S.C. 154(b) by 0 days.

(21) Appl. No.: 16/088,710

(22) PCT Filed: May 8, 2017

(86) PCT No.: PCT/CN2017/083435
§ 371 (c)(1),
(2) Date: Sep. 26, 2018

(87) PCT Pub. No.: WO2017/167315
PCT Pub. Date: Oct. 5, 2017

(65) Prior Publication Data
US 2019/0112480 A1 Apr. 18, 2019

(51) Int. Cl.
C07D 495/04 (2006.01)
C07D 285/14 (2006.01)
C09B 3/82 (2006.01)
C09B 1/00 (2006.01)
C07D 285/02 (2006.01)
C07D 285/00 (2006.01)
H01G 9/20 (2006.01)
C09B 5/00 (2006.01)

(52) U.S. Cl.
CPC .............. *C09B 3/82* (2013.01); *C07D 285/00* (2013.01); *C07D 285/02* (2013.01); *C07D 285/14* (2013.01); *C09B 1/00* (2013.01); *C09B 5/00* (2013.01); *C09B 5/006* (2013.01); *H01G 9/20* (2013.01); *H01G 9/2059* (2013.01); *Y02E 10/542* (2013.01)

(58) Field of Classification Search
CPC ........................... C07D 495/04; C07D 285/14
See application file for complete search history.

(56) References Cited

PUBLICATIONS

Yang et al. Macromolecules 2006, 39, 5696-5704 (Year: 2006).*

* cited by examiner

*Primary Examiner* — Matthew P Coughlin

(57) ABSTRACT

The invention provides an anthracene-based organic dye and a preparation method thereof. The organic dye provided by the invention has a structure of formula (I) or formula (II), wherein $R_a$, $R_b$, and $R_{2-1}$ to $R_{2-4}$ are as defined herein. The organic dye provided by the invention is obtained by modifying an anthracene with $R_a$ and $R_b$ or modifying anthracene-based groups decorated with an aryl group or a heteroaryl group with $R_a$ and $R_b$, thereby the power conversion efficiency of a dye sensitized solar cell is significantly improved when the organic dye prepared according to the present invention is applied in a dye-sensitized solar cell. Furthermore, the preparation method of the organic dye according to the present invention is quite simple together with abundant raw materials and low cost, making it possible to be commercialized.

12 Claims, 2 Drawing Sheets

ANTHRACENE-BASED ORGANIC DYES AND PREPARATION METHODS THEREOF

CROSS REFERENCE TO RELATED APPLICATIONS

The present application is a 35 U.S.C. 371 national stage application of PCT International Application No. PCT/CN2017/083435, filed on May 8, 2017, the disclosure of which is hereby incorporated in its entirety by reference.

TECHNICAL FIELD

This invention relates to the field of dye-sensitized solar cells, and particularly to anthracene-based organic dyes and preparation methods thereof.

BACKGROUND ART

Energy and environmental protection are topics of 21th century, and China has been the first energy source-importing country in the world at present. Environmental problems such as fog, haze, and the like accompanying with consumption of fossil energy sources gradually become severe, and it is urgently required to seek clean and sustainable energy sources. The development and use of solar energy, which is a kind of renewable and clean energy source, is one of hot spots in the research area of energy sources.

Much attention has been paid to the dye-sensitized solar cell world widely, which is an important type of solar cells. In 1991, a research team of Grätzel produced a device by adsorbing a trinuclear ruthenium dye $RuL_2(\mu\text{-}(CN)Ru(CN)L'_2)_2$ (L is 2,2'-bipyridin-4,4'-dicarboxylic acid, L'=2,2'-bipyridine) reported by Amadelli et al. on a high-quality $TiO_2$ nanocrystal which was developed by them in several years. A power conversion efficiency of 7.1% was achieved under simulated sunlight, and the research on dye-sensitized solar cells was thereby started. Compared to conventional inorganic semiconductor solar cells, dye-sensitized solar cells have relatively low-cost of production, abundant colors, and good appearance, and may be produced into semitransparent products. Flexible dye-sensitized solar cells can be widely used in daily life due to their relatively lightweight, foldable and windable properties.

At present, dyes used in commercial solar cells are all ruthenium complexes containing the precious metal. However, the resource of ruthenium is insufficient, and the cost of ruthenium-based materials is high, which severely impedes their productions and applications in a large scale, and thereby pure organic dyes have been the general trend. However, only few devices can achieve a power conversion efficiency over 10% produced with pure organic dyes at present. In addition, the complicated synthesis of most of the materials used in high efficient devices hinders the development of the pure organic dyes in dye sensitized solar cells. Furthermore, there are few highly efficient blue dyes, and thus the universality and practicability in application are limited.

SUMMARY OF THE INVENTION

In view of this, one of technical problems to be solved by the invention is to provide an organic dye. The organic dye provided by the invention not only has a simple preparation method, but also has a high power conversion efficiency when being used in a solar cell.

The invention provides an organic dye having a structure of formula (I) or formula (II):

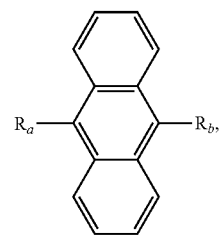

Formula (I)

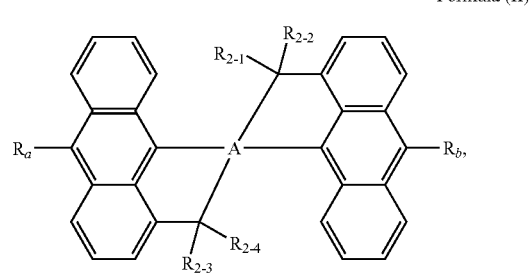

Formula (II)

wherein, $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

$R_b$ is formula ($R_b$-1), formula ($R_b$-2), formula ($R_b$-3), or formula ($R_b$-4):

Formula ($R_b$-1)

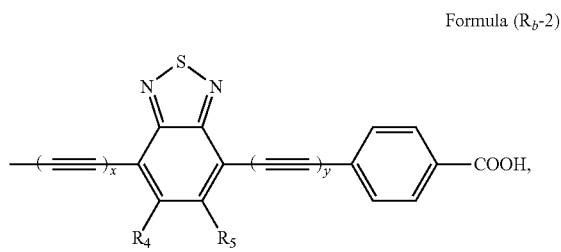

Formula ($R_b$-2)

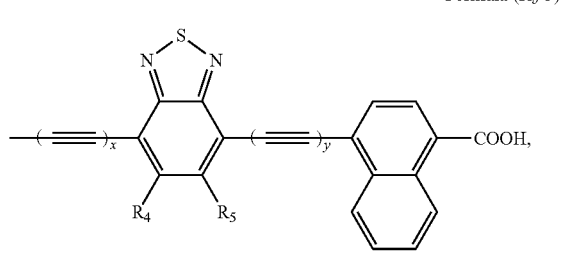

Formula ($R_b$-3)

-continued

Formula (R_b-4)

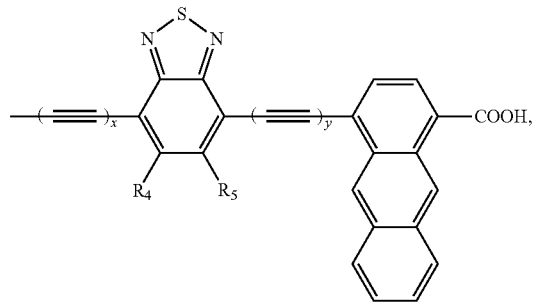

wherein x and y are independently selected from 0 or 1, and both $R_4$ and $R_5$ are H;

A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

$R_{2-1}$, $R_{2-2}$, $R_{2-3}$, and $R_{24}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group.

Preferably, $R_a$ is formula ($R_a$-1), formula ($R_a$-2), formula ($R_a$-3), formula ($R_a$-4), formula ($R_a$-5), formula ($R_a$-6), or formula ($R_a$-7):

Formula (R_a-1)

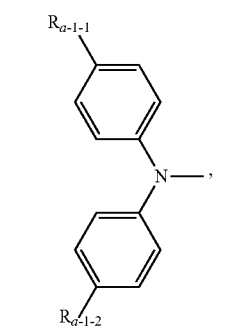

Formula (R_a-2)

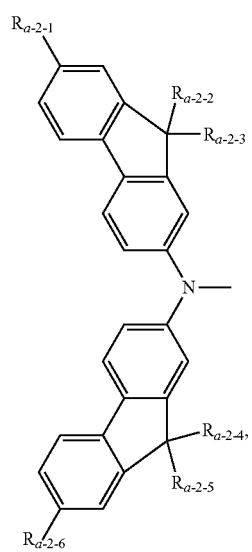

Formula (R_a-3)

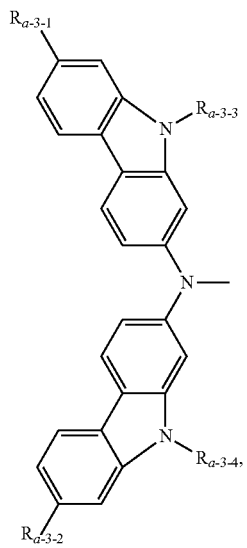

Formula (R_a-4)

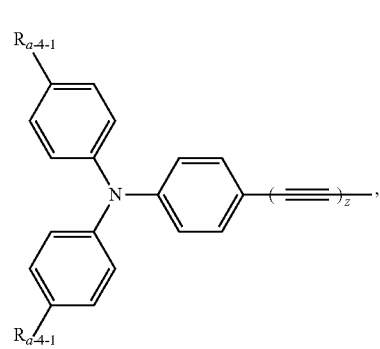

Formula (R_a-5)

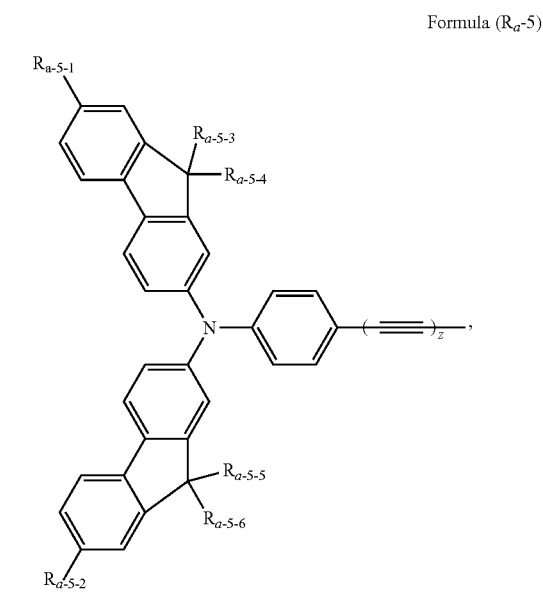

-continued

Formula ($R_a$-6)

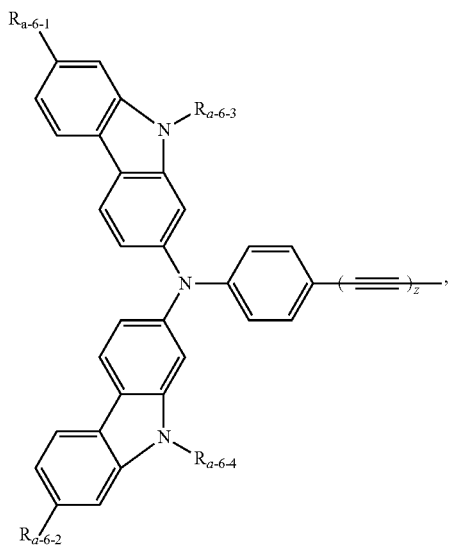

Formula ($R_a$-7)

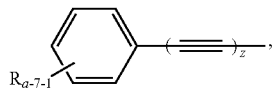

wherein $R_{a-3-3}$, $R_{a-3-4}$, $R_{a-6-3}$, and $R_{a-6-4}$ are independently selected from H or a $C_1$-$C_{36}$ alkyl group;

$R_{a-1-1}$, $R_{a-1-2}$, $R_{a-2-1}$, $R_{a-2-2}$, $R_{a-3-1}$, $R_{a-3-2}$, $R_{a-4-1}$, $R_{a-4-2}$, $R_{a-5-1}$, $R_{a-5-2}$, $R_{a-6-1}$, and $R_{a-6-2}$ are independently selected from H, a $C_1$-$C_{36}$ alkyl group, or a $C_1$-$C_{36}$ alkoxy group;

$R_{a-2-3}$, $R_{a-2-4}$, $R_{a-2-5}$, $R_{a-2-6}$, $R_{a-5-3}$, $R_{a-5-4}$, $R_{a-5-5}$, and $R_{a-5-6}$ are independently selected from H, a $C_1$-$C_{36}$ alkyl group, a phenyl group substituted with a $C_1$-$C_{36}$ alkoxy group, or a phenyl group substituted with a $C_1$-$C_{36}$ alkyl group;

$R_{a-7-1}$ is selected from H, a $C_1$-$C_{36}$ alkyl group, or a $C_1$-$C_{36}$ alkoxy group;

z is 0 or 1.

Preferably, $R_{a-3-3}$, $R_{a-3-4}$, $R_{a-6-3}$, and $R_{a-6-4}$ are independently selected from a $C_6$-$C_{30}$ alkyl group;

$R_{a-1-1}$, $R_{a-1-2}$, $R_{a-2-1}$, $R_{a-2-2}$, $R_{a-3-1}$, $R_{a-3-2}$, $R_{a-4-1}$, $R_{a-4-2}$, $R_{a-5-1}$, $R_{a-5-2}$, $R_{a-6-1}$, and $R_{a-6-2}$ are independently selected from a $C_6$-$C_{30}$ alkyl group or a $C_6$-$C_{30}$ alkoxy group;

$R_{a-2-3}$, $R_{a-2-4}$, $R_{a-2-5}$, $R_{a-2-6}$, $R_{a-5-3}$, $R_{a-5-4}$, $R_{a-5-5}$, and $R_{a-5-6}$ are independently selected from a $C_6$-$C_{30}$ alkyl group, a phenyl group substituted with a $C_6$-$C_{30}$ alkoxy group, or a phenyl group substituted with a $C_6$-$C_{30}$ alkyl group;

$R_{a-7-1}$ is selected from a $C_6$-$C_{30}$ alkyl group or a $C_6$-$C_{30}$ alkoxy group. Preferably, A is formula (A-1), formula (A-2), formula (A-3), formula (A-4), or formula (A-5):

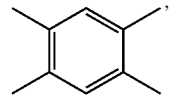

Formula (A-1)

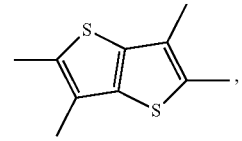

Formula (A-2)

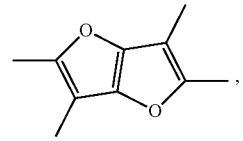

Formula (A-3)

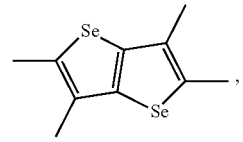

Formula (A-4)

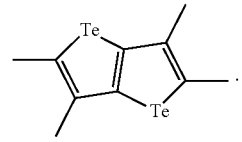

Formula (A-5)

Preferably, $R_{2-1}$, $R_{2-2}$, $R_{2-3}$, and $R_{2-4}$ are independently selected from a $C_6$-$C_{30}$ alkyl group, a phenyl group substituted with a $C_6$-$C_{30}$ alkyl group, or a phenyl group substituted with a $C_6$-$C_{30}$ alkoxy group.

Preferably, the organic dye has the structure of formula (I-1), formula (II-1), or formula (II-2):

Formula (I-1)
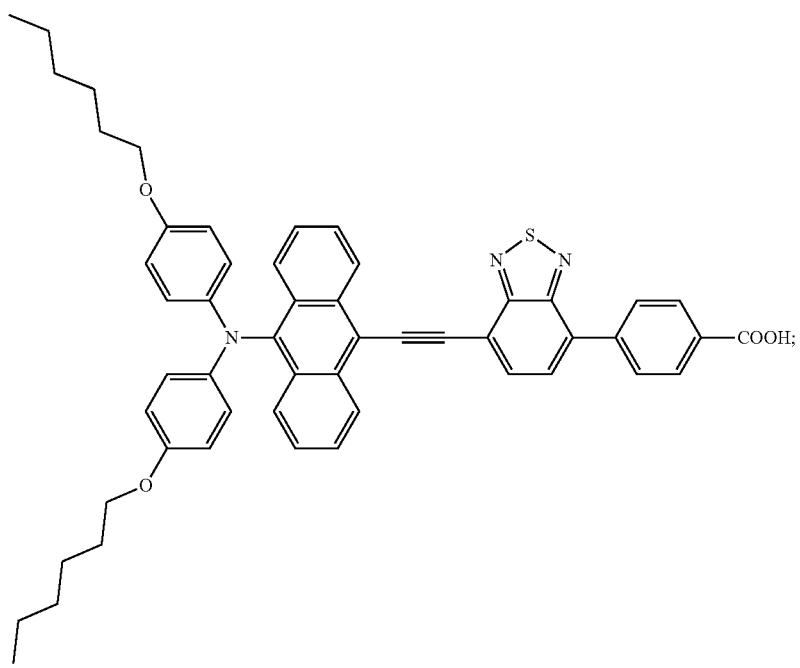
Formula (II-1)
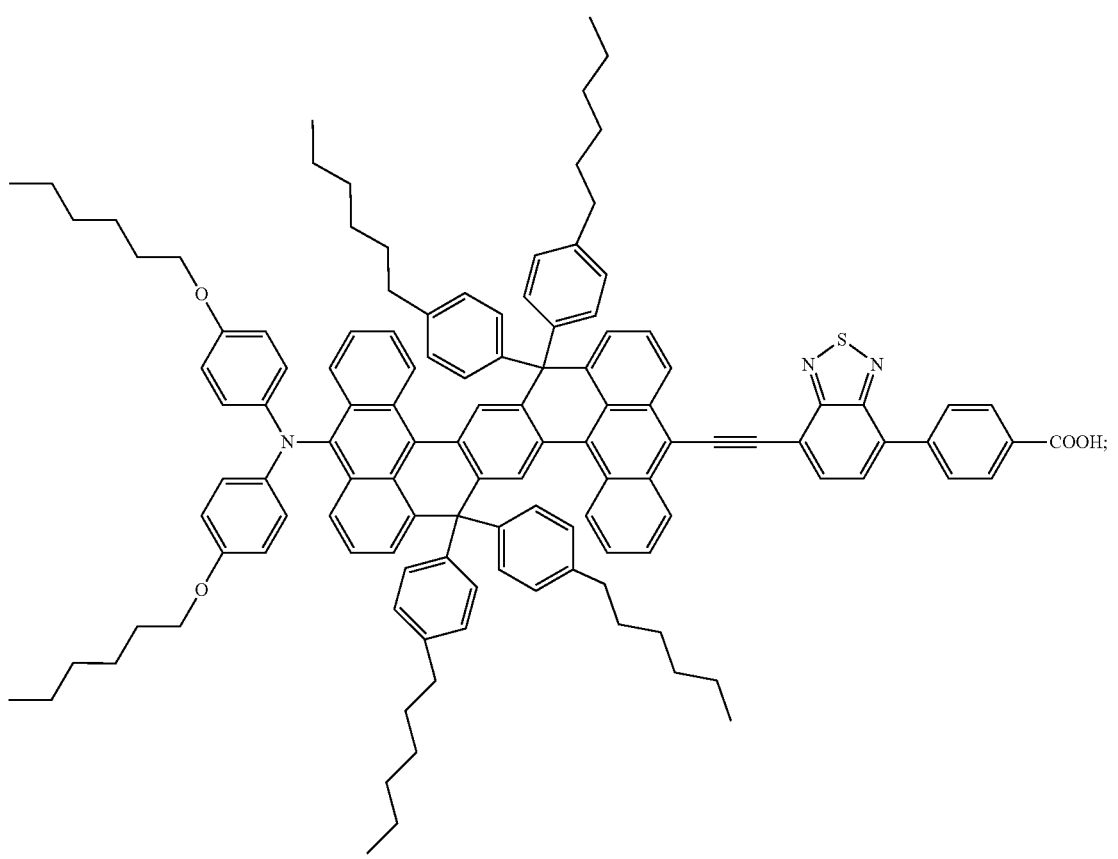

-continued

Formula (II-2)

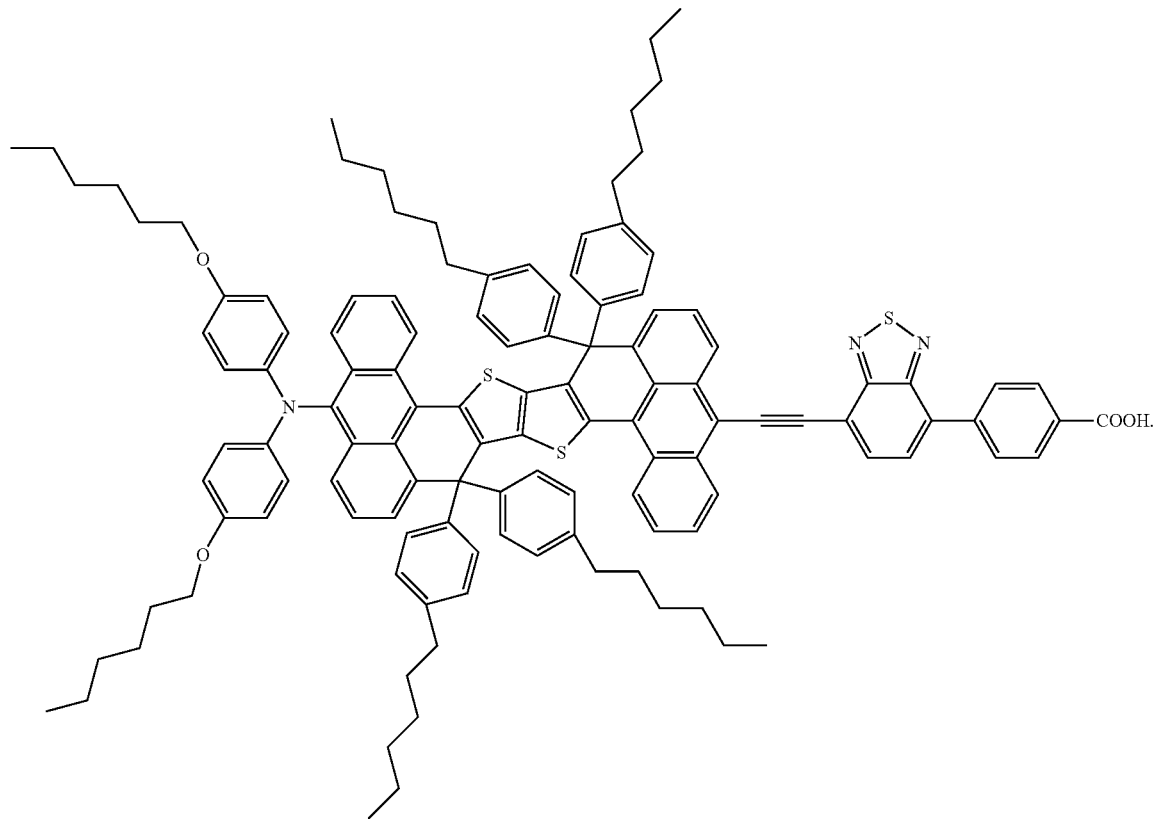

The invention also provides a method for producing the organic dye comprising:

reacting a compound having the structure of formula (III) or formula (IV) with a compound having the structure of formula (V) to obtain a compound having the structure of formula (I) or formula (II);

Formula (III)

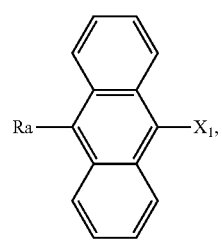

Formula (IV)

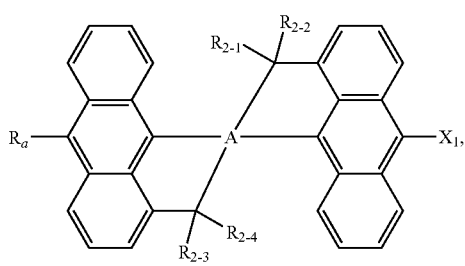

-continued

Formula (V)

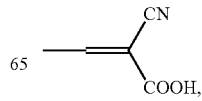

wherein $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

$R_{2-1}$, $R_{2-2}$, $R_{2-3}$, and $R_{2-4}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group;

$R_b$ is formula ($R_b$-1), formula ($R_b$-2), formula ($R_b$-3), or formula ($R_b$-4), Formula ($R_b$-1)

-continued

Formula (R_b-2)

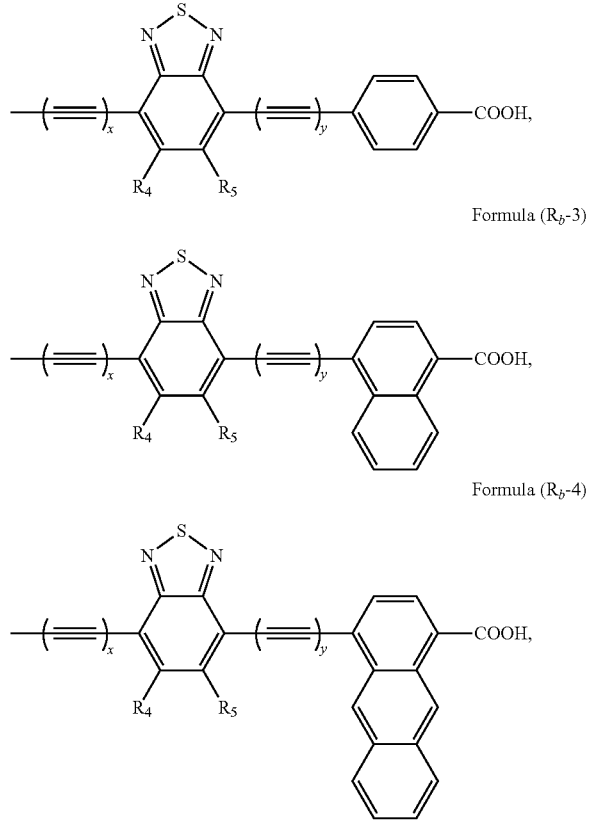

Formula (R_b-3)

Formula (R_b-4)

wherein x and y are independently selected from 0 or 1, and both $R_4$ and $R_5$ are H;

$X_1$ is H, Br, or I.

Preferably, the compound having the structure of formula (IV) is prepared according to a following method:

1) mixing and reacting a compound having the structure of formula (VI), a compound having the structure of formula (VII), and a compound having the structure of formula (VIII) to obtain a compound having the structure of formula (IX);

Formula (VI)

Formula (VII)

Formula (VIII)

Formula (IX)

wherein $R_{6-1}$ and $R_{7-1}$ are independently selected from $Sn(CH_3)_3$—, $Sn(n-Bu)_3$—, or a borate ester group, $R_{8-1}$ and $R_{8-2}$ are independently selected from a $C_1$-$C_8$ alkyl group, $X_2$ and $X_3$ are independently selected from Cl, Br, or I;

2) converting the compound having the structure of formula (IX) to a compound having the structure of formula (IV).

Preferably, the step 2) specifically comprises:

2-1) converting the compound having the structure of formula (IX) to a compound having the structure of formula (X), Formula (X)

2-2) converting the compound having the structure of formula (X) to a compound having the structure of formula (IV).

Preferably, the catalyst used in the step 2-2) is a polymer resin with macroporous and strongly acidic properties.

Compared to the prior art, the invention provides an organic dye having the structure of formula (I) or formula (II). The organic dye provided by the invention is obtained by modifying an anthracene with $R_a$ and $R_b$ or modifying anthracene-based groups decorated with an aryl group or a heteroaryl group with $R_a$ and $R_b$, thereby the power conversion efficiency of a dye sensitized solar cell is significantly improved when the organic dye prepared according to the present invention is applied in a dye-sensitized solar cell. The experimental results reveal that the power conversion efficiency of the solar cell fabricated with the organic dye produced by the present invention can be up to 12.0%.

Furthermore, the preparation method of the organic dye according to the present invention is quite simple together with abundant raw materials and low cost, making it possible to be commercialized.

DETAILED DESCRIPTION

Figure 1:
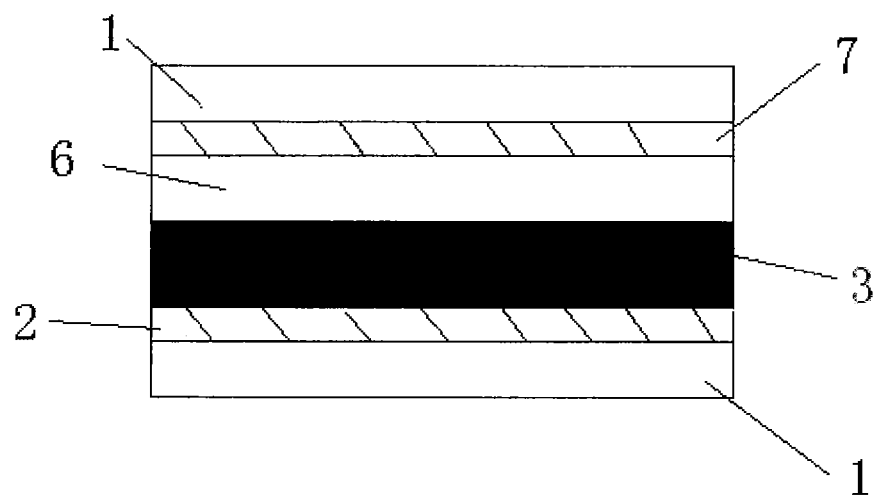
FIG. 1 is a schematic illustration of the device of the dye-sensitized solar cell provided by the invention.

The invention provides an organic dye having the structure of formula (I) or formula (II):

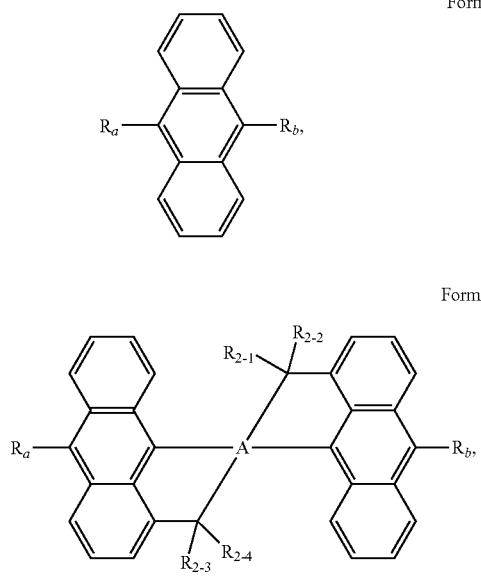

Formula (I)

Formula (II)

wherein, $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

$R_b$ is formula ($R_b$-1), formula ($R_b$-2), formula ($R_b$-3), or formula ($R_b$-4):

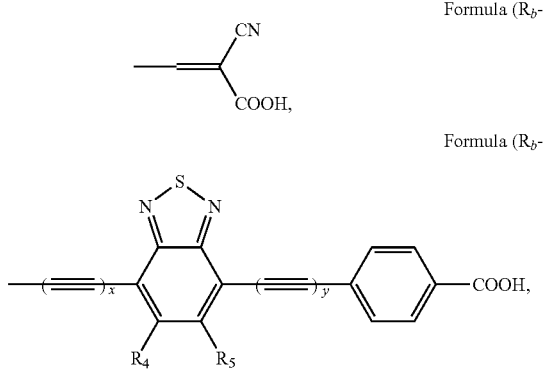

Formula ($R_b$-1)

Formula ($R_b$-2)

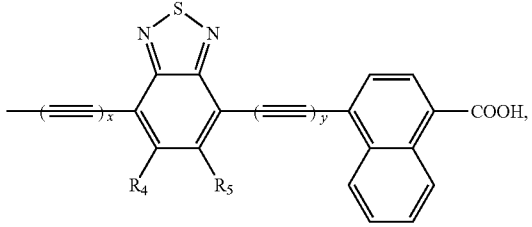

Formula ($R_b$-3)

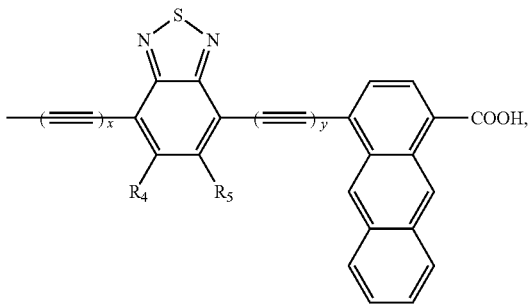

Formula ($R_b$-4)

wherein x and y are independently selected from 0 or 1, and both $R_4$ and $R_5$ are H;

A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

$R_{2-1}$, $R_{2-2}$, $R_{2-3}$, and $R_{2-4}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group.

In the invention, the terms "alkyl group", "alkoxy group", "aryl group", "heteroaryl group", and "hydrocarbyl group" have the meanings as commonly understood by those skilled in the art respectively.

According to the invention, $R_a$ is preferably an amino group substituted with a $C_{12}$-$C_{35}$ aryl group, an amino group substituted with a $C_{12}$-$C_{35}$ heteroaryl group, an unsaturated hydrocarbyl group substituted with a $C_{12}$-$C_{35}$ aryl group, an unsaturated hydrocarbyl group substituted with a $C_{12}$-$C_{35}$ heteroaryl group, a phenyl group substituted with a $C_5$-$C_{30}$ alkyl group, or a phenyl group substituted with a $C_5$-$C_{30}$ alkoxy group. More preferably, $R_a$ is an amino group substituted with a $C_{18}$-$C_{30}$ aryl group, an amino group substituted with a $C_{18}$-$C_{30}$ heteroaryl group, an unsaturated hydrocarbyl group substituted with a $C_{18}$-$C_{30}$ aryl group, an unsaturated hydrocarbyl group substituted with a $C_{18}$-$C_{30}$ heteroaryl group, a phenyl group substituted with a $C_{10}$-$C_{20}$ alkyl group, or a phenyl group substituted with a $C_{10}$-$C_{20}$ alkoxy group. Most preferably, $R_a$ is formula ($R_a$-1), formula ($R_a$-2), formula ($R_a$-3), formula ($R_a$-4), formula ($R_a$-5), formula ($R_a$-6), or formula ($R_a$-7):

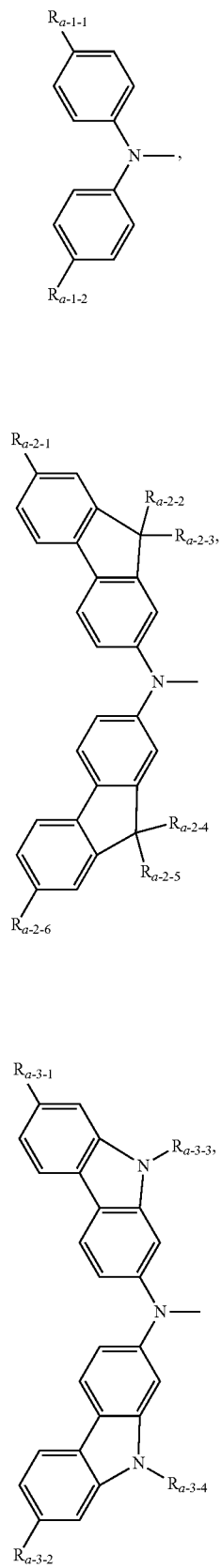
Formula (R$_a$-1)
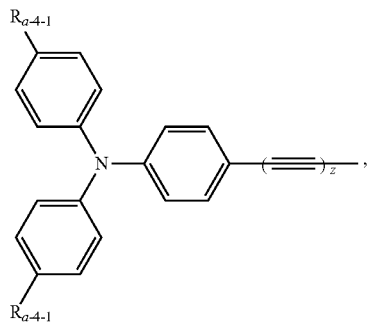
Formula (R$_a$-4)
Formula (R$_a$-2)
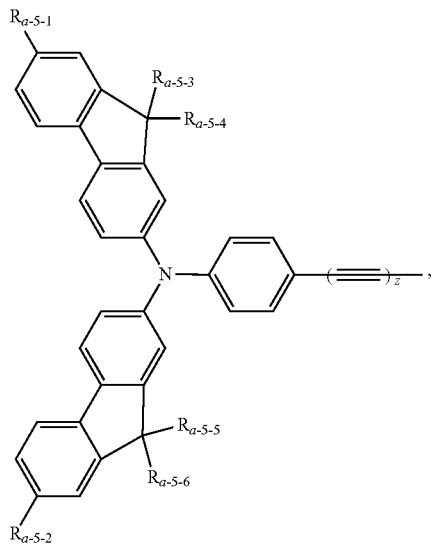
Formula (R$_a$-5)
Formula (R$_a$-3)
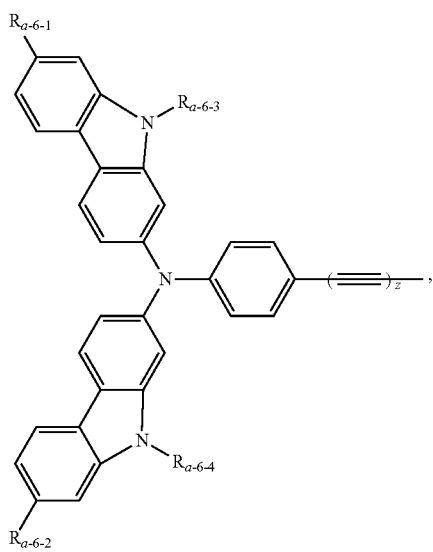
Formula (R$_a$-6)
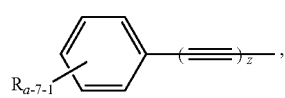
Formula (R$_a$-7)
wherein R$_{a\text{-}3\text{-}3}$, R$_{a\text{-}3\text{-}4}$, R$_{a\text{-}6\text{-}3}$, and R$_{a\text{-}6\text{-}4}$ are independently selected from H or a C$_1$-C$_{36}$ alkyl group;

$R_{a-1-1}$, $R_{a-1-2}$, $R_{a-2-1}$, $R_{a-2-2}$, $R_{a-3-1}$, $R_{a-3-2}$, $R_{a-4-1}$, $R_{a-4-2}$, $R_{a-5-1}$, $R_{a-5-2}$, $R_{a-6-1}$, and $R_{a-6-2}$ are independently selected from H, a $C_1$-$C_{36}$ alkyl group, or a $C_1$-$C_{36}$ alkoxy group;

$R_{a-2-3}$, $R_{a-2}R_{a-2-5}$, $R_{a-2-6}$, $R_{a-5-3}$, $R_{a-5-4}$, $R_{a-5-5}$, and $R_{a-5-6}$ are independently selected from H, a $C_1$-$C_{36}$ alkyl group, a phenyl group substituted with a $C_1$-$C_{36}$ alkoxy group, or a phenyl group substituted with a $C_1$-$C_{36}$ alkyl group;

$R_{a-7-1}$ is selected from H, a $C_1$-$C_{36}$ alkyl group, or a $C_1$-$C_{36}$ alkoxy group;

z is 0 or 1.

According to the invention, $R_{a-3-3}$ is preferably a $C_5$-$C_{30}$ alkyl group, more preferably a $C_7$-$C_{20}$ alkyl group, and most preferably a $C_{10}$-$C_{15}$ alkyl group; $R_{a-3-4}$ is preferably a $C_5$-$C_{30}$ alkyl group, more preferably a $C_7$-$C_{20}$ alkyl group, and most preferably a $C_{10}$-$C_{15}$ alkyl group; $R_{a-6-3}$ is preferably a $C_5$-$C_{30}$ alkyl group, more preferably a $C_7$-$C_{20}$ alkyl group, and most preferably a $C_{10}$-$C_{15}$ alkyl group; $R_{a-6-4}$ is preferably a $C_5$-$C_{30}$ alkyl group, more preferably a $C_7$-$C_{20}$ alkyl group, and most preferably a $C_{10}$-$C_{15}$ alkyl group.

$R_{a-1-1}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; $R_{a-2-1}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; $R_{a-3-1}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; $R_{a-4-1}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; $R_{a-5-1}$ is preferably a $C_5$-$C_{30}$ alkyl group or a $C_5$-$C_{30}$ alkoxy group, more preferably a $C_7$-$C_{20}$ alkyl group or a C7-C20 alkoxy group, and most preferably a $C_{10}$-$C_{15}$ alkyl group or a $C_{10}$-$C_{15}$ alkoxy group; $R_{a-5-2}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; R is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group; $R_{a-6-2}$ is preferably a $C_5$-$C_{30}$ alkyl group or a $C_5$-$C_{30}$ alkoxy group, more preferably a $C_7$-$C_{20}$ alkyl group or a $C_7$-$C_{20}$ alkoxy group, and most preferably a $C_{10}$-$C_{15}$ alkyl group or a $C_{10}$-$C_{15}$ alkoxy group.

$R_{a-2-3}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-2-4}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-2-5}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-2-6}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-5-3}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-5-4}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-5-5}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group; $R_{a-5-6}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group.

$R_{a-7-1}$ is preferably a $C_5$-$C_{30}$ alkyl group, a phenyl group substituted with a $C_5$-$C_{30}$ alkoxy group, or a phenyl group substituted with a $C_5$-$C_{30}$ alkyl group, more preferably a $C_7$-$C_{20}$ alkyl group, a phenyl group substituted with a $C_7$-$C_{20}$ alkoxy group, or a phenyl group substituted with a $C_7$-$C_{20}$ alkyl group, and most preferably a $C_{10}$-$C_{15}$ alkyl group, a phenyl group substituted with a $C_{10}$-$C_{15}$ alkoxy group, or a phenyl group substituted with a $C_{10}$-$C_{15}$ alkyl group.

According to the invention, A is preferably a $C_{10}$-$C_{20}$ aryl group, a $C_6$-$C_{20}$ oxygen-containing heteroaryl group, a $C_6$-$C_{20}$ sulfur-containing heteroaryl group, a $C_6$-$C_{20}$ selenium-containing heteroaryl group, or a $C_6$-$C_{20}$ tellurium-containing heteroaryl group, more preferably a $C_{14}$-$C_{18}$ aryl group, a $C_{12}$-$C_{18}$ oxygen-containing heteroaryl group, a $C_{12}$-$C_{18}$ sulfur-containing heteroaryl group, a $C_{12}$-$C_{18}$ selenium-containing heteroaryl group, or a $C_{12}$-$C_{18}$ tellurium-containing heteroaryl group, and most preferably formula (A-1), formula (A-2), formula (A-3), formula (A-4), or formula (A-5),

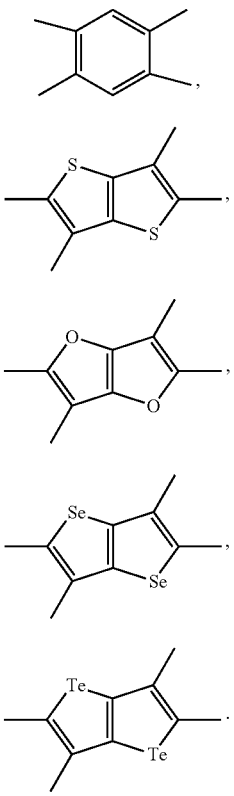

Formula (A-1)

Formula (A-2)

Formula (A-3)

Formula (A-4)

Formula (A-5)

According to the invention, $R_{2-1}$ is preferably a $C_6$-$C_{30}$ alkyl group, a phenyl group substituted with a $C_6$-$C_{30}$ alkyl group, or a phenyl group substituted with a $C_6$-$C_{30}$ alkoxy group, more preferably a $C_8$-$C_{20}$ alkyl group, a phenyl group substituted with a $C_8$-$C_{20}$ alkyl group, or a phenyl group substituted with a $C_8$-$C_{20}$ alkoxy group, and most preferably a $C_{10}$-$C_{15}$ alkyl group, a phenyl group substituted with a $C_{10}$-$C_{15}$ alkyl group, or a phenyl group substituted with a $C_{10}$-$C_{15}$ alkoxy group; $R_{2-2}$ is preferably a $C_6$-$C_{30}$ alkyl group, a phenyl group substituted with a $C_6$-$C_{30}$ alkyl group, or a phenyl group substituted with a $C_6$-$C_{30}$ alkoxy group, more preferably a $C_8$-$C_{20}$ alkyl group, a phenyl group substituted with a $C_8$-$C_{20}$ alkyl group, or a phenyl group substituted with a $C_8$-$C_{20}$ alkoxy group, and most preferably a $C_{10}$-$C_{15}$ alkyl group, a phenyl group substituted with a $C_{10}$-$C_{15}$ alkyl group, or a phenyl group substituted with a $C_{10}$-$C_{15}$ alkoxy group; $R_{2-3}$ is preferably a $C_6$-$C_{30}$ alkyl group, a phenyl group substituted with a $C_6$-$C_{30}$ alkyl group, or a phenyl group substituted with a $C_6$-$C_{30}$ alkoxy group, more preferably a $C_8$-$C_{20}$ alkyl group, a phenyl group substituted with a $C_8$-$C_{20}$ alkyl group, or a phenyl group substituted with a $C_8$-$C_{20}$ alkoxy group, and most preferably a $C_{10}$-$C_{15}$ alkyl group, a phenyl group substituted with a $C_{10}$-$C_{15}$ alkyl group, or a phenyl group substituted with a $C_{10}$-$C_{15}$ alkoxy group; $R_{2-4}$ is preferably a $C_6$-$C_{30}$ alkyl group, a phenyl group substituted with a $C_6$-$C_{30}$ alkyl group, or a phenyl group substituted with a $C_6$-$C_{30}$ alkoxy group, more preferably a $C_8$-$C_{20}$ alkyl group, a phenyl group substituted with a $C_8$-$C_{20}$ alkyl group, or a phenyl group substituted with a $C_8$-$C_{20}$ alkoxy group, and most preferably a $C_{10}$-$C_{15}$ alkyl group, a phenyl group substituted with a $C_{10}$-$C_{15}$ alkyl group, or a phenyl group substituted with a $C_{10}$-$C_{15}$ alkoxy group.

More particularly, the organic dye has the structure of formula (I-1), formula (II-1), or formula (II-2):

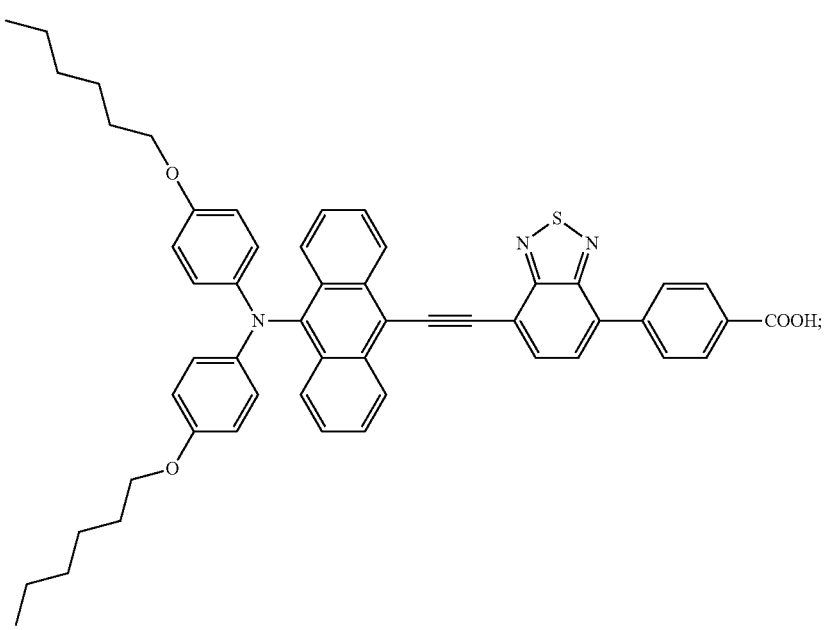

Formula (I-1)

Formula (II-1)
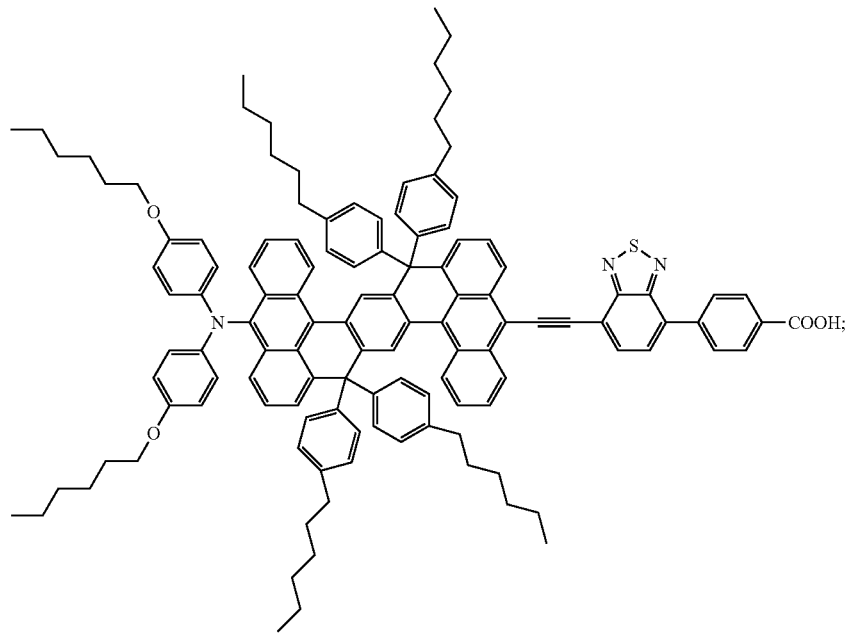
Formula (II-2)
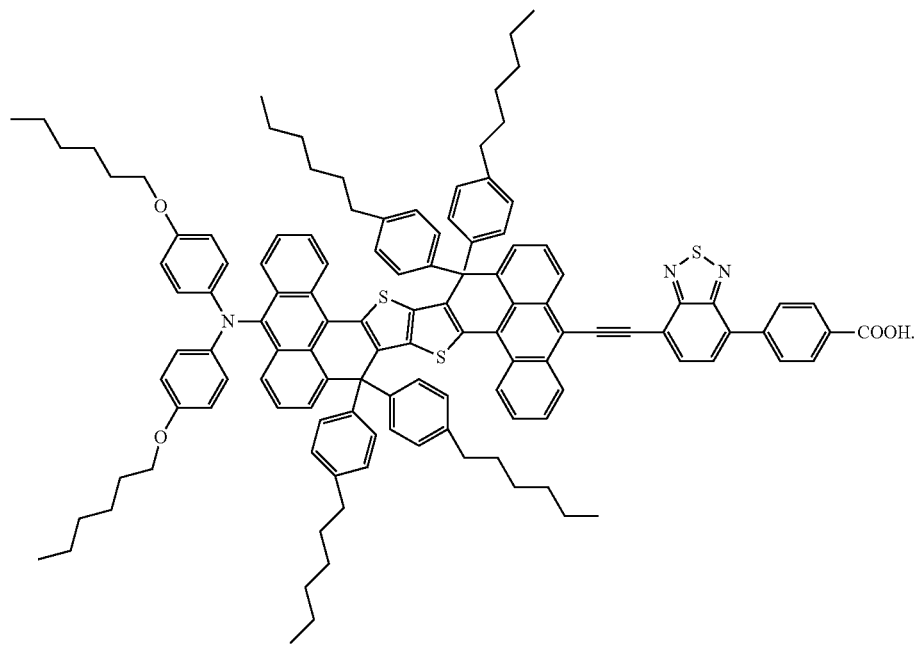
The invention also provides a preparation method for the organic dye of the invention, comprising: reacting a compound having the structure of formula (III) or formula (IV) with a compound having the structure of formula (V) to obtain a compound having the structure of formula (I) or formula (II);

Formula (III)

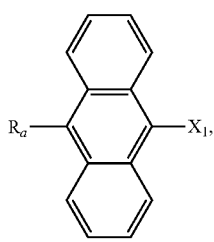

Formula (IV)

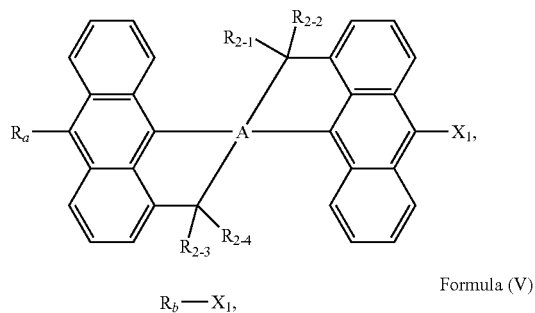

Formula (V)

$R_b$—$X_1$, $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

$R_b$ is formula ($R_b$-1), formula ($R_b$-2), formula ($R_b$-3), or formula ($R_b$-4), Formula ($R_b$-1)

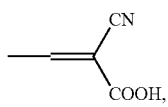

Formula ($R_b$-2)

Formula ($R_b$-3)

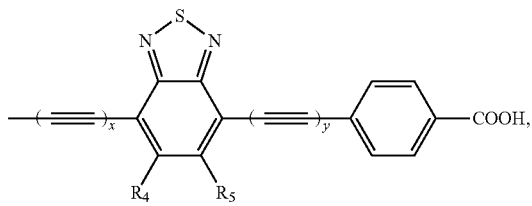

Formula ($R_b$-4)

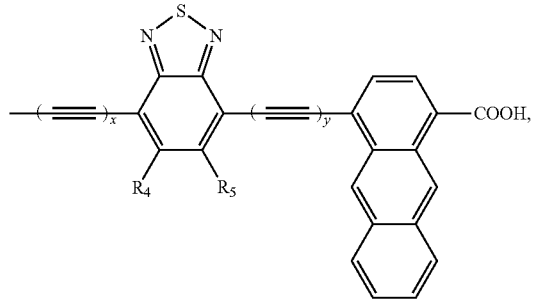

wherein x and y are independently selected from 0 or 1, and both $R_4$ and $R_5$ are H;

A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

$R_{2-1}$, $R_{2-2}$, $R_{2-3}$, and $R_{24}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group;

$X_1$ is H, Br, or I.

According to the method of the present invention, a compound having the structure of formula (III) or formula (IV) is reacted with a compound having the structure of formula (V) to obtain a compound having the structure of formula (I) or formula (II). The reaction condition is not particularly limited in the present invention. In the method of the invention, N-bromosuccinimide (NBS) is preferably used to activate a compound having the structure of formula (III) or formula (IV), and the activated compound then is reacted with a compound having the structure of formula (V) to obtain a compound having the structure of formula (I) or formula (II). Here, in the reaction of the activated compound with a compound having the structure of formula (V), the catalyst used is preferably cesium carbonate, and a toluene mixed solution of $Pd_2(dba)_3$ and an organic phosphine ligand $P(t-Bu)_3$.

Here, the selection for the substituents in compounds having the structure of formula (III), formula (IV), and formula (V) is the same as that for the substituents in the organic dye described above.

In the method of the invention, the source of the raw material is not particularly limited, as long as it can be prepared or obtained by a method generally known in the art, wherein the compound having the structure of formula (IV) is preferably prepared according to the following method:

1) mixing and reacting a compound having the structure of formula (VI), a compound having the structure of formula (VII), and a compound having the structure of formula (VIII) to obtain a compound having the structure of formula (IX);

Formula (VI)

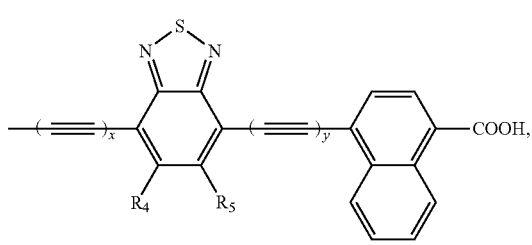

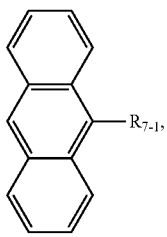

Formula (VII)

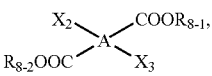

Formula (VIII)

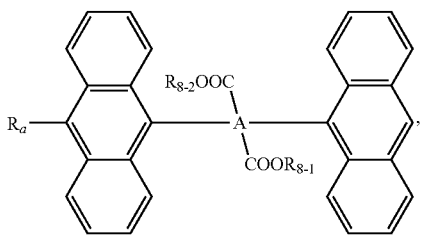

Formula (IX)

wherein $R_{6-1}$ and $R_{7-1}$ are independently selected from $Sn(CH_3)_3—$, $Sn(n\text{-}Bu)_3—$, or a borate ester group, $R_{8-1}$ and $R_{8-2}$ are independently selected from a $C_1\text{-}C_8$ alkyl group, $X_2$ and $X_3$ are independently selected from Cl, Br, or I;

2) converting the compound having the structure of formula (IX) to a compound having the structure of formula (IV).

According to the method of the invention, a compound having the structure of formula (VI), a compound having the structure of formula (VII), and a compound having the structure of formula (VIII) are mixed and reacted to obtain a compound having the structure of formula (IX); wherein the amount of each raw material used in the reaction is not particularly limited in the method of the invention, and a suitable amount may be selected by those skilled in the art according to the practical requirement; the catalyst used in the reaction is preferably tris(dibenzylideneacetone) dipalladium and $P(t\text{-}Bu)_3$, or tris(dibenzylideneacetone) dipalladium, $P(t\text{-}Bu)_3$, and $CsCO_3$, or $Pd(OAc)_2$ and an organic phosphine ligand 2-bicyclohexylphosphine-2',6'-dimethoxybiphenyl (Sphos). The solvent used in the reaction is preferably toluene, 1,4-dioxane or a mixed solvent of 1,4-dioxane and water. The temperature of the reaction is preferably 80-130° C.

According to the method of the invention, the compound having the structure of formula (IX) is converted to a compound having the structure of formula (IV), which is preferably prepared according to the following method:

2-1) converting the compound having the structure of formula (IX) to a compound having the structure of formula (X),

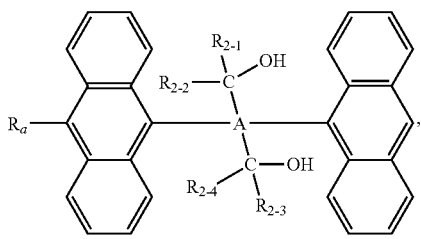

Formula (X)

2-2) converting the compound having the structure of formula (X) to a compound having the structure of formula (IV).

Here, the reaction procedure of the step 2-1) of the invention is not particularly limited, and it can be carried out by a reaction procedure generally known in the art. The catalyst used in the step 2-2) is preferably a polymer resin with macroporous and strongly acidic sulfonic acid type, and more preferably a solid acid catalyst Amberlyst 15.

The invention provides an organic dye having the structure of formula (I) or formula (II). The organic dye produced by the invention is obtained by modifying anthracene with $R_a$ and $R_b$ or modifying anthracene-based groups decorated with an aryl group or a heteroaryl group with $R_a$ and $R_b$, thereby the power conversion efficiency of a dye sensitized solar cell is significantly improved when the organic dye prepared according to the present invention is applied in a dye-sensitized solar cell. Furthermore, the preparation method of the organic dye according to the present invention is quite simple with abundant raw materials and low cost, making it possible to be commercialized.

Hereinafter, the present invention will be described clearly and fully with reference to the technical solutions of examples. Obviously, the examples described are only a part of the examples of the present invention, rather than all of the examples. Based on the examples in the present invention, all other examples obtainable for those skilled in the art without any inventive work will fall into the protection scope of the invention.

Example 1

Preparation of Compound Having the Structure of Formula (I-1)

Reaction Scheme 1

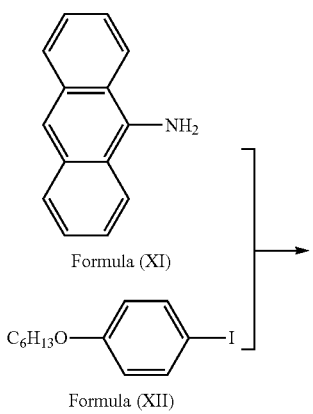

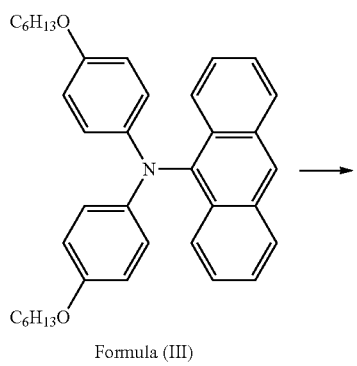

Formula (III)

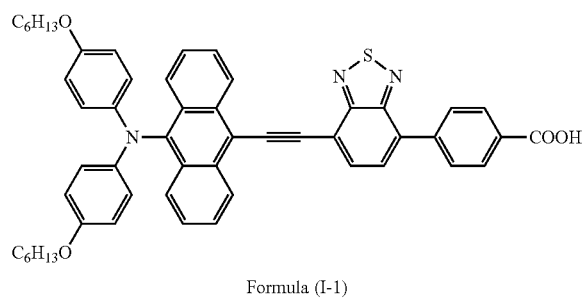

Formula (I-1)

The compound having the structure of formula (XI) was synthesized according to the reference document (Hirano, K.; Urban, S.; Wang, C.; Glorius, Frank. *Org. Lett.* 2009, 11, 1019). The compound having the structure of formula (XII) was synthesized according to the reference document (Hiroko, Y.; Ikuyoshi, T.; Kazuchika, O.; Takeshi, E. *Mol. Cryst. Liq. Cryst. A* 2001, 369, 47). Butyl 4-(7-ethynylbenzo[c][1,2,5]thiadiazol-4-yl)benzoate (namely Triple-bond benzothiadiazole butyl benzoate) was synthesized according to the reference document (L. Yang, Y. Ren, Z. Yao, C. Yan, W. Ma and P. Wang, *J. Phys. Chem. C,* 2015, 119, 980). The sources of other raw material compounds, solvents, and catalysts in the preparation process of dyes are not particularly limited, and they can be commercially available or prepared with the methods well known in the art.

Synthesis of the Compound Having the Structure of Formula (III):

In a dry Schlenk flask, the compound having the structure of formula (XI) (2.77 g), the compound having the structure of formula (XII) (10.87 g), and sodium tert-butoxide (4.12 g) were dissolved in 100 mL toluene. The catalyst $Pd_2(dba)_3$ (524 mg) and $P(t-Bu)_3$ (2.17 mL 10% by mass solution in toluene) were added in a glove box of a nitrogen atmosphere. The reaction system was stirred at reflux overnight.

After completion of the reaction, the reaction system was cooled to room-temperature. 30 mL water was added, and the mixed solution was extracted with chloroform three times. The organic phases were combined, and dried with anhydrous sodium sulfate. The desiccant was removed by filtration. The filtrate was concentrated, and then purified by column chromatography with toluene/petroleum ether (boiling range=60-90° C.) (1/2 in volume ratio) as an eluent to obtain 5.31 g of the compound having the structure of formula (III) with a yield of 68%.

The structure of the resultant compound of formula (III) was characterized by nuclear magnetic resonance (NMR), mass spectrometric and elemental analysis. The results were as follows:

$^1$H NMR (500 MHz, CDCl3) δ: 8.46 (s, 1H), 8.15 (d, J=8.8 Hz, 2H), 8.04 (d, J=8.4 Hz, 2H), 7.44 (t, J=6.7 Hz, 2H), 7.38 (t, J=8.6 Hz, 2H), 6.96 (d, J=3.5 Hz, 4H), 6.76-6.69 (m, 4H), 3.85 (t, J=6.5 Hz, 4H), 1.75-1.69 (m, 4H), 1.44-1.39 (m, 4H), 1.32-1.30 (m, 8H), 0.90 (t, J=6.9 Hz, 6H).

$^{13}$C NMR (125 MHz, CDCl3) δ: 156.51, 153.53, 142.05, 138.06, 133.00, 131.38, 130.89, 130.07, 130.03, 128.97, 128.21, 127.20, 126.44, 125.51, 124.73, 121.25, 115.25, 108.78, 71.46, 68.39, 31.73, 29.49, 25.88, 22.74, 22.19, 14.17.

The results of high-resolution mass spectrometric analysis: 545.32938.

The results of elemental analysis: C, 83.62%; H, 7.95%; N, 2.56%.

Synthesis of the Compound Having the Structure of Formula (I-1):

In a three-neck round bottom flask, the intermediate compound of the formula (III) (2 g) was dissolved in tetrahydrofuran (THF) (30 mL). NBS (684 mg) was added to the reaction mixture, which was stirred at room temperature for 10 minutes. 30 mL water was added, and the mixed solution was extracted with chloroform three times (3×15 mL). The organic phases were combined, and dried with anhydrous sodium sulfate. The desiccant was removed by filtration.

The filtrate was concentrated, and then purified by column chromatography with toluene/petroleum ether (boiling range=60-90° C.) (1/5 in volume ratio) as an eluent. The crude product obtained was directly used in the next reaction step.

In a dry Schlenk flask, the crude product obtained above (411 mg), butyl 4-(7-ethynylbenzo[c][1,2,5]thiadiazol-4-yl)benzoatethe (330 mg) and $Cs_2CO_3$ (234 mg) were dissolved in dioxane (20 mL). The catalyst $Pd_2(dba)_3$ (54 mg) and $P(t-Bu)_3$ (0.3 mL 10% by mass solution in toluene) were added in a glove box of a nitrogen atmosphere. The reaction system was stirred at reflux for 6 h.

After completion of the reaction, the reaction system was cooled to room-temperature. 30 mL of water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/1 in volume ratio) as an eluent to obtain a black powder, which was a butyl ester compound.

In a three-neck round bottom flask, the butyl ester compound obtained above (466 mg) and KOH (297 mg) was dissolved in a solvent mixture of 15 mL THF and 5 mL $H_2O$. The reaction mixture was refluxed for 8 h.

After completion of the reaction, the reaction system was cooled to room-temperature. 20 mL aqueous solution of phosphoric acid (0.1 mol/L) was added, and the mixed solution was extracted with chloroform three times. The organic phases were combined and dried with anhydrous sodium sulfate. The desiccant was removed by filtration. The filtrate was concentrated, and then was purified by column chromatography with trichloromethane/methanol (20/1 in volume ratio) as an eluent to obtain 354 mg of the compound of formula (I-1) with a yield of 81%.

The structure of the resultant compound having the structure of formula (I-1) was characterized by NMR, mass spectrometric and elemental analysis. The results were as follows:

$^1$H NMR (500 MHz, THF-d8) δ: 9.05 (d, J=8.7 Hz, 2H), 8.24☐8.19 (m, 7H), 8.01 (d, J=7.4 Hz, 1H), 7.64 (t, J=7.5 Hz, 2H), 7.44 (t, J=7.8 Hz, 2H), 6.95 (d, J=9.1 Hz, 4H), 6.71 (d, J=9.1 Hz, 4H), 3.84 (t, J=6.4 Hz, 4H), 1.70☐1.67 (m, 2H), 1.46☐1.41 (m, 4H), 1.33☐1.29 (m, 10H), 0.89 (t, J=6.9 Hz, 6H).

$^{13}$C NMR (125 MHz, THF-d8) δ: 167.21, 156.44, 154.81, 153.84, 142.73, 141.72, 141.01, 135.00, 134.00, 132.86, 131.31, 129.87, 129.02, 127.59, 127.29, 125.94, 122.09, 117.67, 117.12, 115.72, 98.52, 94.31, 32.67, 32.39, 30.45, 27.8326.54, 26.21, 23.33, 14.26, 14.19.

The results of high-resolution mass spectrometric analysis: 823.34199.

The results of elemental analysis: C, 77.24%; H, 5.98%; N, 5.11%.

Example 2

Preparation of Compound Having Structure of Formula (II-1)

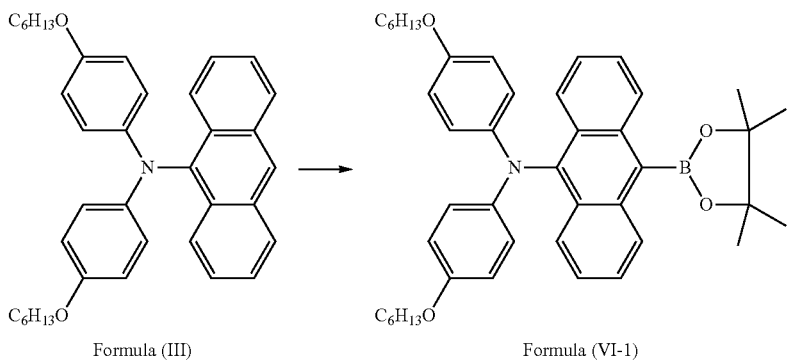

Reaction Scheme 2

Formula (III) → Formula (VI-1)

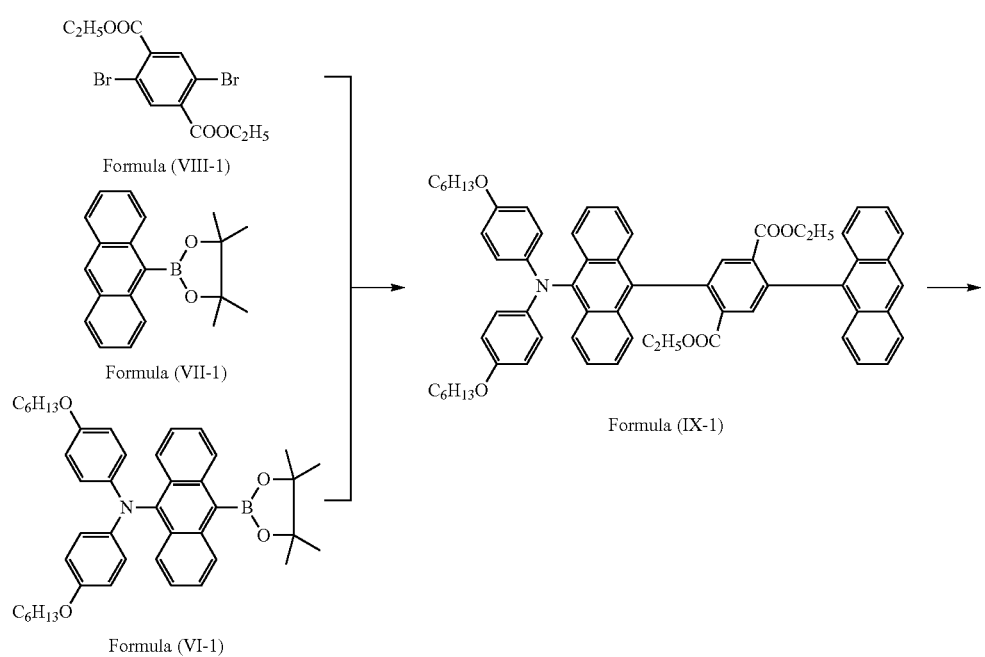

Formula (VIII-1)
Formula (VII-1)
Formula (VI-1)
Formula (IX-1)

-continued

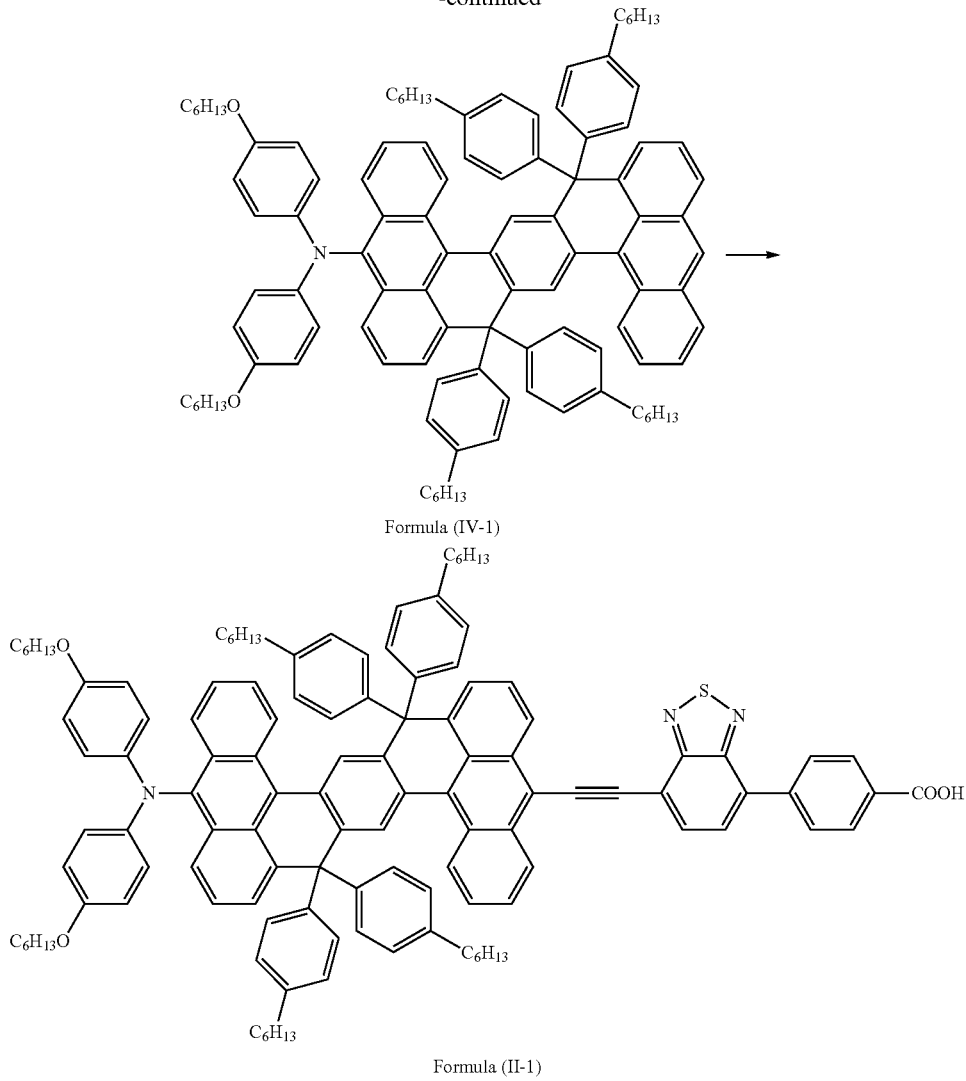

Formula (IV-1)

Formula (II-1)

The compound of formula (VII-1) was synthesized according to the reference document (Kawamorita, S.; Ohmiya, H.; Iwai, T.; Sawamura, M. *Angew. Chem. Int. Ed.* 2011, 50, 8363). The sources of other raw material compounds, solvents, and catalysts in the preparation process of dyes are not particularly limited, and can be commercially available or prepared by a method well known in the art.

Synthesis of a Compound of Formula (VI-1):

In three-neck round bottom flask, the compound of formula (III) (10.0 g) was dissolved in 50 mL THF, and N-bromosuccinimide (3.42 g) was added slowly. The reaction system was stirred in dark for 10 min at room temperature. After completion of the reaction, 30 mL of water was added, and then was extracted with chloroform three times (3×15 mL). The organic phases were combined, dried with anhydrous sodium sulfate. The desiccant was removed by filtration. The filtrate was concentrated, and then purified by column chromatography with toluene/petroleum ether (boiling range=60-90° C.) (1/5 in volume ratio) as an eluent. The crude product obtained was directly used in the next reaction step.

In a dry Schlenk flask, the crude product obtained above (11 g), bis(pinacolato)diboron (8.97 g), and potassium acetate (51.97 g) were dissolved in 150 mL toluene. Then the catalyst Pd(dppf)Cl$_2$ (650 mg) was added under an argon atmosphere. The reaction system was stirred at reflux for 6 h. After completion of the reaction, the reaction system was cooled to room-temperature. 30 mL water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/3 in volume ratio) as an eluent to obtain 9.48 g of the compound of formula (VI-1) with a yield of 80%.

The structure of the resultant compound of formula (VI-1) was characterized by NMR, mass spectrometric and elemental analysis. The results were as follows:

$^1$H NMR (500 MHz, CDCl$_3$) δ: 8.43 (d, J=8.8 Hz, 2H), 8.15 (d, J=8.7 Hz, 2H), 7.45 (t, J=7.7 Hz, 2H), 7.35 (t, J=8.7 Hz, 2H), 6.93 (d, J=9.1 Hz, 4H), 6.68 (d, J=9.1 Hz, 4H), 3.84 (t, J=6.6 Hz, 4H), 1.74-1.69 (m, 4H), 1.43-1.39 (m, 4H), 1.34-1.28 (m, 10H), 0.89 (t, J=6.9 Hz, 6H).

$^{13}$C NMR (125 MHz, CDCl$_3$) δ: 153.49, 141.92, 140.36, 137.17, 130.35, 128.99, 126.15, 125.88, 125.15, 121.18, 115.19, 84.74, 68.36, 31.73, 29.48, 25.87, 22.73, 14.17.

The results of high-resolution mass spectrometric analysis: 671.41600.

The results of elemental analysis: C, 78.67%; H, 8.11%; N, 2.10%.

Synthesis of a Compound Having a Structure of Formula (IX-1):

In a three-neck round bottom flask, the compound of formula (VI-1) (4 g), the compound of formula (VII-1) (1.81 g), and the compound of formula (VIII-1) (2.26 g) were dissolved in a mixed solvent of dioxane/water (60 mL, 5/1 in volume ratio). The catalyst palladium acetate (68 mg), 2-bicyclohexylphosphine-2',6'-dimethoxybiphenyl (Sphos) (123 mg), and potassium phosphate (6.32 g) were added under an argon atmosphere. The reaction system was stirred at reflux overnight. After completion of the reaction, the reaction system was cooled to room-temperature. 30 mL water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (2/1 in volume ratio) as an eluent to obtain 2.41 g of the compound of formula (IX-1) with a yield of 43%.

The structure of the resultant compound having the structure of formula (IX-1) was characterized by NMR, mass spectrometric and elemental analysis. The results were as follows:

$^1$H NMR (400 MHz, THF-d$_8$) δ: 8.63 (s, 1H), 8.31□8.26 (m, 4H), 8.12 (d, J=8.1 Hz, 2H), 7.77□7.72 (m, 4H), 7.51□7.41 (m, 8H), 7.06□7.00 (m, 4H), 6.74 (d, J=8.4 Hz, 4H), 3.87 (t, J=6.2 Hz, 4H), 3.89□3.86 (m, 2H), 3.56□3.55 (m, 2H), 1.45 (br, 4H), 1.33 (br, 10H), 0.90 (br, 6H), 0.34 (t, J=7.1 Hz, 3H), 0.24 (t, J=14.1 Hz, 3H).

$^{13}$C NMR (125 MHz, THF-d$_8$) δ: 166.02, 166.00, 154.66, 154.52, 142.85, 142.75, 140.05, 139.91, 139.09, 136.71, 136.61, 136.15, 135.97, 135.69, 135.59, 132.30, 132.22, 131.31, 130.96, 129.14, 127.69, 126.86, 126.66, 126.39, 126.32, 125.71, 125.50, 122.12, 121.61, 115.71, 115.62, 61.11, 60.91, 32.40, 32.39, 30.17, 14.21, 13.35, 13.06.

The results of high-resolution mass spectrometric analysis: 941.46314.

The results of elemental analysis: C, 81.60%; H, 6.75%; N, 1.50%.

Synthesis of a Compound of Formula (IV-1):

In a flame-dried three-neck round bottom flask, the compound of formula (IX-1) (2 g) was dissolved in 30 mL THF. Under the protection of argon gas, p-hexylphenylmagnesium bromide solution (6.36 mL, 2M in THF) was added. The reaction system was stirred at 90° C. for 6 h. After completion of the reaction, the reaction system was cooled to 0° C. 20 mL water was added, and the mixed solution was extracted with chloroform three times. The organic phases were combined and dried with anhydrous sodium sulfate. The desiccant was removed by filtration. The filtrate was concentrated and directly used in the next reaction step.

In a dry three-neck round bottom flask, the above obtained crude product was dissolved in 30 mL toluene. Then the solid acid catalyst Amberlyst 15 (1.00 g) was added. The mixture was stirred at reflux for 8 h under the protection of argon gas. After completion of the reaction, the reaction system was cooled to room-temperature. 30 mL water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/3 in volume ratio) as an eluent to obtain 2.45 g of the compound of formula (IV-1) with a yield of 79%.

The structure of the resultant compound having the structure of formula (IV-1) was characterized by NMR, mass spectrometric and elemental analysis. The results were as follows:

$^1$H NMR (500 MHz, THF-d$_8$) δ: 8.36 (s, 1H), 8.09-7.92 (m, 8H), 7.45-7.14 (m, 9H), 7.01 (br, 10H), 6.89 (br, 10H), 6.68 (br, 4H), 3.84 (br, 4H), 2.57 (br, 8H), 1.60 (br, 6H), 1.30 (br, 42H), 0.87 (br, 18H).

$^{13}$C NMR (125 MHz, THF-d$_8$) δ: 154.56, 145.28, 145.08, 143.43, 143.28, 143.25, 143.05, 142.77, 141.52, 141.48, 138.84, 133.75, 133.36, 133.26, 132.50, 131.79, 130.97, 130.33, 129.39, 129.18, 128.25, 128.03, 127.46, 126.29, 126.00, 125.86, 125.72, 125.44, 125.42, 124.08, 121.93, 115.66, 60.83, 36.16, 35.99, 32.68, 32.39, 32.09, 32.06, 30.54, 30.53, 30.45, 30.38, 30.36, 30.30, 30.15, 30.10, 30.08, 30.05, 29.93, 27.84, 27.83, 26.55, 26.23, 23.38, 23.34, 23.28, 14.24, 14.22.

The results of high-resolution mass spectrometric analysis: 1462.92076.

The results of elemental analysis: C, 88.67%; H, 8.21%; N, 0.95%.

Synthesis of a Compound of Formula (II-1):

In a round bottom flask, the compound of formula (IV-1) (750 mg) was dissolved in 30 mL THF. N-bromosuccinimide (96 mg) was added slowly. The reaction system was stirred for 6 h in dark at room temperature. After completion of the reaction, 30 mL water was added, and then the mixed solution was extracted with chloroform three times (3×15 mL). The organic phases were combined, dried with anhydrous sodium sulfate. The desiccant was removed by filtration. The filtrate was concentrated, and then purified by column chromatography with toluene/petroleum ether (boiling range=60-90° C.) (1/3 in volume ratio) as an eluent. The crude product obtained was directly used in the next reaction step.

In a dry Schlenk flask, the crude product obtained above (833 mg), butyl 4-(7-ethynylbenzo[c][1,2,5]thiadiazol-4-yl)benzoatethe (363 mg) and Cs$_2$CO$_3$ (192 mg) were dissolved in dioxane (30 mL) The catalyst Pd$_2$(dba)$_3$ (29 mg) and P(t-Bu)$_3$ (0.17 mL 10% by mass solution in toluene) were added in a glove box of a nitrogen atmosphere. The reaction system was stirred at reflux overnight.

After completion of the reaction, the reaction system was cooled to room-temperature. 30 mL of water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/1 in volume ratio) as an eluent to obtain a black powder, which was a butyl ester compound.

In a three-neck round bottom flask, the butyl ester compound obtained above (791 mg) and KOH (246 mg) was dissolved in a solvent mixture of THF/H$_2$O (20 mL, 3/1 in volume ratio). The reaction mixture was refluxed for 10 h.

After completion of the reaction, the reaction system was cooled to room-temperature. 20 mL aqueous solution of phosphoric acid (0.1 M) was added, and the mixed solution was extracted with chloroform three times. The organic phases were combined and dried with anhydrous sodium sulfate. The desiccant was removed by filtration. The filtrate was concentrated, and then was purified by column chromatography with trichloromethane/methanol (20/1 in volume ratio) as an eluent to obtain 767 mg of the compound having the structure of formula (II-1) with a yield of 81%.

The structure of the resultant compound having the structure of formula (II-1) was characterized by NMR, mass spectrometric and elemental analysis. The results were as follows:

$^1$H NMR (500 MHz, THF-$d_8$) δ: 8.95 (d, J=9.2 Hz, 1H), 8.91 (d, J=8.5 Hz, 1H), 8.21☐8.17 (m, 4H), 8.13☐8.08 (m, 4H), 8.05 (d, J=8.8 Hz, 1H), 8.00 (d, J=5.6 Hz, 2H), 7.92 (d, J=7.4 Hz, 1H), 7.64 (t, J=7.1 Hz, 1H), 7.48 (t, J=6.9 Hz, 1H), 7.37 (t, J=8.6 Hz, 1H), 7.24☐7.14 (m, 4H), 7.10☐7.03 (m, 11H), 6.93☐6.91 (m, 10H), 6.70☐6.67 (m, 4H), 3.84 (t, J=6.5 Hz, 4H), 2.58☐2.57 (m, 8H), 1.70☐1.68 (m, 2H), 1.59 (br, 8H), 1.47☐1.41 (m, 4H), 1.34☐1.30 (m, 34H), 0.91☐0.86 (m, 18H).

$^{13}$C NMR (125 MHz, THF-$d_8$) δ: 167.21, 156.40, 154.61, 153.78, 143.83, 143.45, 142.78, 141.73, 141.68, 141.62, 139.21, 134.67, 134.03, 133.75, 133.21, 133.06, 132.69, 132.50, 132.39, 131.51, 130.97, 130.92, 130.42, 130.34, 130.32, 129.85, 129.52, 129.31, 128.97, 128.45, 128.33, 128.09, 127.76, 127.72, 127.60, 127.09, 126.83, 126.35, 126.23, 126.06, 125.89, 124.18, 121.98, 117.78, 117.46, 115.68, 99.07, 95.16, 68.47, 67.74, 60.95, 60.82, 36.16, 35.99, 32.68, 32.39, 32.09, 32.07, 30.54, 30.52, 30.45, 30.36, 30.29, 30.16, 30.10, 30.07, 30.05, 29.94, 29.92, 27.82, 26.55, 26.22, 25.62, 23.38, 23.34, 23.29, 23.28, 14.26, 14.23, 14.22, 14.21.

The results of high-resolution mass spectrometric analysis: 1740.93722.

The results of elemental analysis: C, 84.83%; H, 7.25%; N, 2.40%.

Example 3

Preparation of Compound of Formula (II-2)

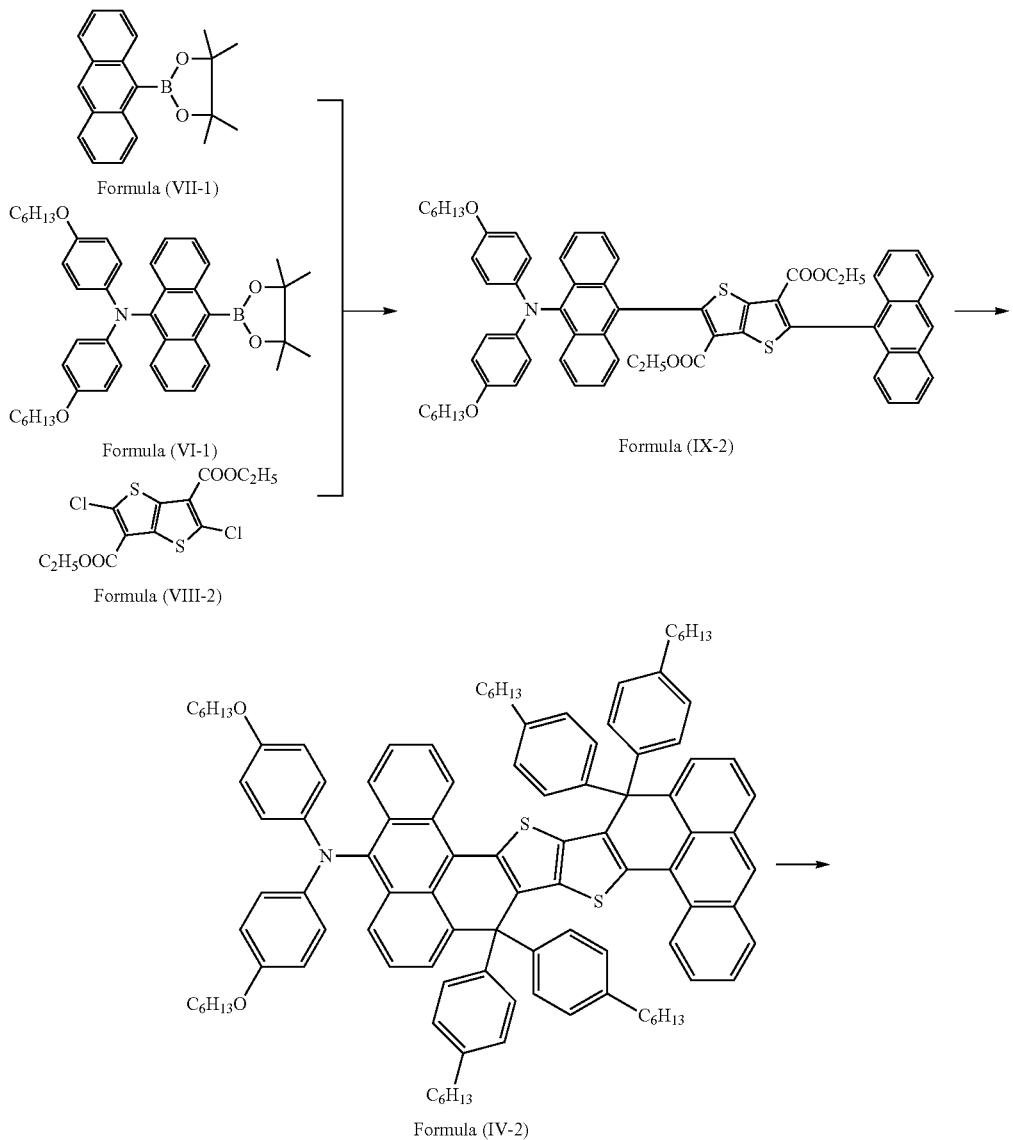

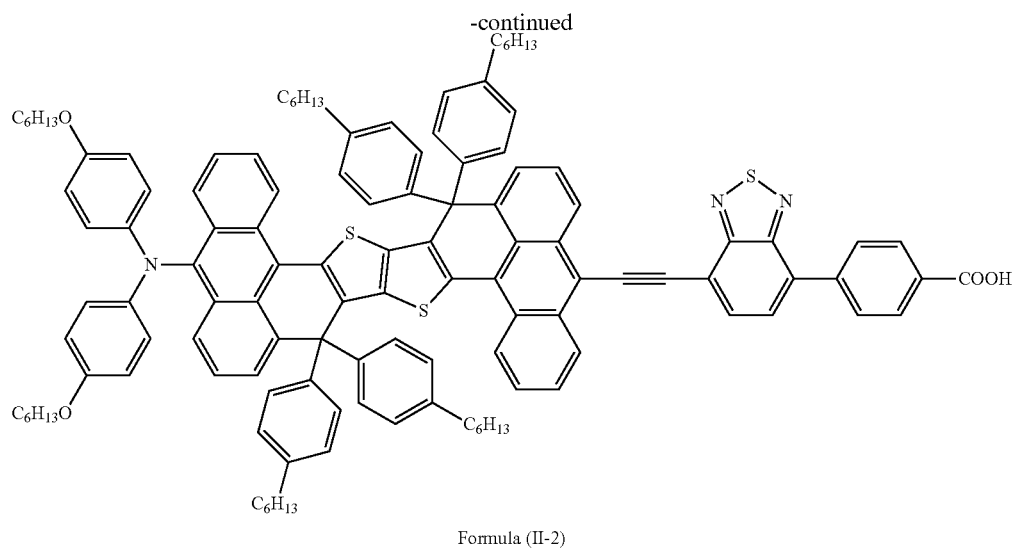

Formula (II-2)

The compound of formula (VIII-2) was synthesized according to the reference document (Kunz, T.; Knochel, P. *Chem. Eur. J.* 2011, 17, 866). The sources of other raw material compounds, solvents, and catalysts in the preparation process of dyes are not particularly limited, and can be commercially available or prepared by a method well known in the art.

Synthesis of a Compound Having a Structure of Formula (IX-2):

In a three-neck round bottom flask, the compound having the structure of formula (VI-1) (4 g), the compound having the structure of formula (VII-1) (2.26 g), and the compound having the structure of formula (VIII-2) (2.10 g) were dissolved in a mixed solvent of dioxane/water (60 mL, 5/1 in volume ratio). The catalyst palladium acetate (68 mg), 2-bicyclohexylphosphine-2',6'-dimethoxybiphenyl (Sphos) (123 mg), and potassium phosphate (6.32 g) were added under an argon atmosphere. The reaction system was stirred at reflux overnight. After completion of the reaction, the reaction system was cooled to room-temperature. 30 mL water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (2/1 in volume ratio) as an eluent to obtain 3.47 g of the compound having the structure of formula (IX-2) with a yield of 58%.

The structure of the resultant compound having the structure of formula (IX-2) was characterized by NMR, mass spectrometric and elemental analysis. The results were as follows:

$^1$H NMR (500 MHz, CDCl$_3$) δ: 8.63 (s, 1H), 8.26 (d, J=7.6 Hz, 2H), 8.10 (d, J=8.0 Hz, 2H), 7.95□7.90 (m, 4H), 7.54□7.47 (m, 4H), 7.46□7.41 (m, 4H), 7.05 (t, J=8.8 Hz, 4H), 6.78 (d, J=9.1 Hz, 2H), 6.74 (d, J=9.1 Hz, 2H), 3.92□3.85 (m, 8H), 1.77□1.72 (m, 4H), 1.45□1.41 (m, 4H), 1.34□1.32 (m, 8H), 0.90 (t, J=6.6 Hz, 6H), 0.59□0.54 (m, 6H).

$^{13}$C NMR (125 MHz, CDCl) δ: 162.05, 161.81, 153.72, 153.70, 150.42, 149.96, 142.09, 142.03, 140.05, 138.49, 138.38, 132.78, 131.50, 131.23, 130.43, 128.81, 128.59, 127.53, 127.50, 126.98, 126.46, 126.43, 126.34, 126.24, 125.43, 125.29, 125.07, 124.94, 121.46, 121.41, 115.40, 115.29, 68.43, 60.97, 60.80, 31.74, 29.49, 25.89, 22.74, 14.18, 13.38.

The results of high-resolution mass spectrometric analysis: 1003.39188.

The results of elemental analysis: C, 76.53%; H, 6.13%; N, 1.38%.

Synthesis of a Compound of Formula (IV-2):

In a flame-dried three-neck round bottom flask, the compound having the structure of formula (IX-3) (3 g) was dissolved in 10 mL THF. Under the protection of argon gas, p-hexylphenylmagnesium bromide solution (8.97 mL, 2M in THF) was added. The reaction system was stirred at 90° C. for 6 h. After completion of the reaction, the reaction system was cooled to 0° C. 20 mL water was added, and the mixed solution was extracted with chloroform three times. The organic phases were combined and dried with anhydrous sodium sulfate. The desiccant was removed by filtration. The filtrate was concentrated and directly used in the next reaction step.

In a dry three-neck round bottom flask, the above obtained crude product was dissolved in 30 mL toluene. Then the solid acid catalyst Amberlyst 15 (1.5 g) was added. The mixture was stirred at reflux for 6 h under the protection of argon gas. After completion of the reaction, the reaction system was cooled to room-temperature. 30 mL water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/3 in volume ratio) as an eluent to obtain 3.79 g of the compound having the structure of formula (IV-2) with a yield of 79%.

The structure of the resultant compound having the structure of formula (IV-2) was characterized by NMR, mass spectrometric and elemental analysis. The results were as follows:

$^1$H NMR (400 MHz, THF-d$_8$) δ: 8.67 (d, J=8.8 Hz, 1H), 8.61 (d, J=7.3 Hz, 1H), 8.35 (s, 1H), 8.13 (d, J=8.4 Hz, 2H), 7.96-7.92 (m, 2H), 7.47-7.36 (m, 4H), 7.34-7.22 (m, 4H), 7.07 (br, 16H), 6.92 (d, J=9.0 Hz, 4H), 6.68 (d, J=8.9 Hz,

4H), 3.84 (t, J=6.2 Hz, 4H), 2.61-2.56 (m, 8H), 1.60-1.59 (m, 8H), 1.44 (br, 6H), 1.34-1.30 (m, 20H), 1.27-1.26 (m, 14H), 0.90-0.84 (m, 18H).

$^{13}$C NMR (150 MHz, THF-d$_8$) b: 154.62, 144.43, 143.58, 143.00, 142.77, 142.35, 142.28, 141.95, 141.82, 138.68, 138.04, 137.68, 137.33, 133.16, 132.17, 132.02, 131.40, 130.92, 130.34, 129.86, 129.76, 129.66, 128.62, 128.53, 128.50, 128.14, 127.92, 127.33, 127.06, 126.87, 126.74, 126.63, 126.33, 126.07, 126.02, 125.79, 125.69, 125.45, 124.52, 121.90, 115.66, 68.48, 67.71, 58.90, 36.23, 32.44, 32.38, 32.36, 30.52, 30.44, 30.37, 30.29, 30.15, 29.97, 29.92, 27.83, 26.54, 26.22, 25.59, 23.33, 23.24, 23.22, 14.22.

The results of high-resolution mass spectrometric analysis: 1524.84854.

The results of elemental analysis: C, 85.06%; H, 7.74%; N, 0.91%.

Synthesis of a Compound of Formula (II-2):

In a round bottom flask, the compound having the structure of formula (IV-2) (866 mg) was dissolved in 30 mL THF. N-bromosuccinimide (102 mg) was added slowly. The reaction system was stirred for 5 h at room temperature. After completion of the reaction, 30 mL water was added, and then the mixed solution was extracted with chloroform three times (3×15 mL). The organic phases were combined, dried with anhydrous sodium sulfate. The desiccant was removed by filtration. The filtrate was concentrated, and then purified by column chromatography with toluene/petroleum ether (boiling range=60-90° C.) (1/2 in volume ratio) as an eluent. The crude product obtained was directly used in the next reaction step.

In a dry Schlenk flask, the crude product obtained above (866 mg), butyl 4-(7-ethynylbenzo[c][1,2,5]thiadiazol-4-yl)benzoate (363 mg) and Cs$_2$CO$_3$ (192 mg) were dissolved in dioxane (30 mL). The catalyst Pd$_2$(dba)$_3$ (29 mg) and P(t-Bu)$_3$ (0.17 mL 10% by mass solution in toluene) were added in a glove box of a nitrogen atmosphere. The reaction system was stirred at reflux overnight.

After completion of the reaction, the reaction system was cooled to room-temperature. 30 mL of water was added, and the mixed solution was extracted with chloroform three times. The organic phases were combined and dried with anhydrous sodium sulfate. The desiccant was removed by filtration. The filtrate was concentrated, and then was purified by column chromatography with toluene/petroleum ether (boiling range=60-90° C.) (1/1 in volume ratio) as an eluent to obtain a black powder, which was a butyl ester compound.

In a three-neck round bottom flask, the butyl ester compound obtained above (874 mg) and KOH (263 mg) was dissolved in a solvent mixture of THF/H$_2$O (20 mL, 3/1 in volume ratio). The reaction mixture was refluxed for 12 h.

After completion of the reaction, the reaction system was cooled to room-temperature. 20 mL aqueous solution of phosphoric acid (0.1 M) was added, and the mixed solution was extracted with chloroform three times. The organic phases were combined and dried with anhydrous sodium sulfate. The desiccant was removed by filtration. The filtrate was concentrated, and then was purified by column chromatography with trichloromethane/methanol (20/1 in volume ratio) as an eluent to obtain 850 mg of the compound having the structure of formula (II-2) with a yield of 81%.

The structure of the resultant compound having the structure of formula (II-2) was characterized by NMR, mass spectrometric and elemental analysis. The results were as follows:

$^1$H NMR (500 MHz, THF-d$_8$) δ: 8.99 (t, J=8.2 Hz, 2H), 8.65 (dd, J$_1$=5.3 Hz, J$_2$=8.3 Hz, 2H), 8.18□8.14 (m, 6H), 8.01 (d, J=7.4 Hz, 1H), 7.81 (d, J=7.4 Hz, 1H), 7.69 (t, J=7.2 Hz, 1H), 7.59 (t, J=7.0 Hz, 1H), 7.44□7.41 (m, 1H), 7.39□7.31 (m, 4H), 7.25 (d, J=6.7 Hz, 1H), 7.12□7.07 (m, 16H), 6.93 (d, J=9.1 Hz, 4H), 6.69 (d, J=9.1 Hz, 4H), 3.84 (t, J=6.5 Hz, 4H), 2.59 (t, J=7.7 Hz, 8H), 1.62□1.56 (m, 8H), 1.47⌣1.41 (m, 4H), 1.34□1.24 (m, 36H), 0.91□0.82 (m, 18H).

$^{13}$C NMR (125 MHz, THF-d$_8$) δ: 167.21, 156.35, 154.65, 153.71, 144.31, 144.17, 143.47, 143.41, 143.05, 142.75, 142.53, 142.43, 142.08, 141.69, 139.21, 139.05, 138.70, 137.67, 137.61, 134.13, 133.61, 133.24, 132.53, 132.01, 131.47, 131.38, 130.94, 130.90, 130.39, 130.33, 130.31, 130.10, 129.89, 129.84, 128.97, 128.88, 128.83, 128.77, 128.65, 128.59, 128.42, 128.30, 127.73, 127.41, 127.18, 127.03, 126.95, 126.91, 126.81, 126.76, 126.71, 126.36, 126.13, 126.08, 125.57, 124.58, 121.93, 117.69, 117.43, 115.66, 99.47, 95.39, 68.46, 67.73, 59.09, 58.88, 44.62, 36.23, 35.98, 32.67, 32.47, 32.43, 32.38, 32.36, 30.53, 30.51, 30.44, 30.36, 30.34, 30.28, 30.14, 30.09, 30.06, 30.04, 29.98, 29.91, 27.83, 27.81, 26.54, 26.21, 25.61, 23.33, 23.27, 23.21, 14.25, 14.21, 14.19.

The results of high-resolution mass spectrometric analysis: 1801.86743.

The results of elemental analysis: C, 81.92%; H, 6.86%; N, 2.34%.

Example 4

An organic dye-sensitized solar cell was fabricated according to the reference document (*Energy Environ. Sci.*, 2010, 3, 1924), and the specific procedure was as follows:

The organic dyes obtained in Examples 1-3 (i.e., the compound having the structure of formula (I-1), the compound having the structure of formula (II-1), and the compound having the structure of formula (II-2)) were prepared into a 150 μmol/L ethanol/toluene (7/3 in volume ratio) solution, respectively.

A bilayer membrane electrode with TiO$_2$-structure was immerged in the solution described above for 12 hours to adsorb the organic dye molecule as a photo-sensitizer onto the TiO$_2$ membrane. The electrode was taken out, and then a glass electrode coated with nanoplatinum was sealed annularly by a hot melt method. At last, an electrolyte was filled into the gap between the two electrodes to construct a dye-sensitized solar cell.

Figure 2:
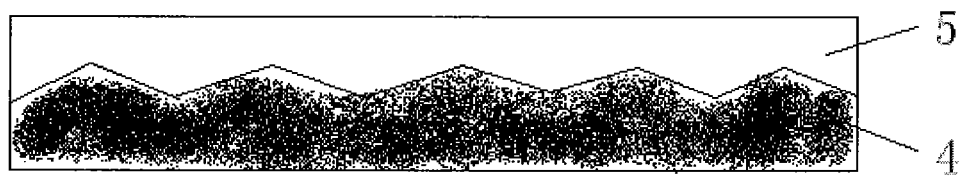
FIG. 2 is a schematic illustration of a light absorbing layer in the dye-sensitized solar cell provided by the invention.
Figure 3:
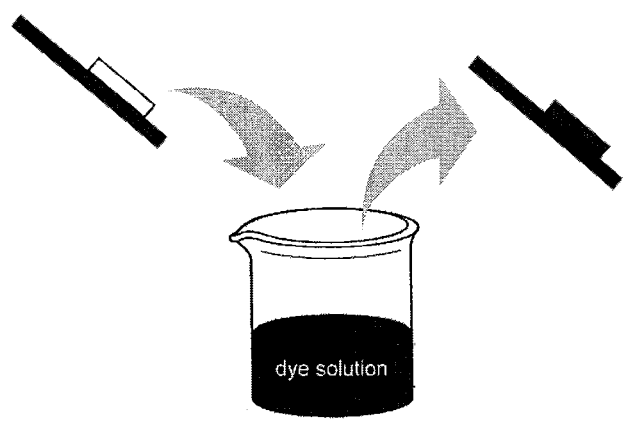
FIG. 3 is a process flow chart of the manufacture of the dye-sensitized solar cell provided by the invention.
Figure 3:
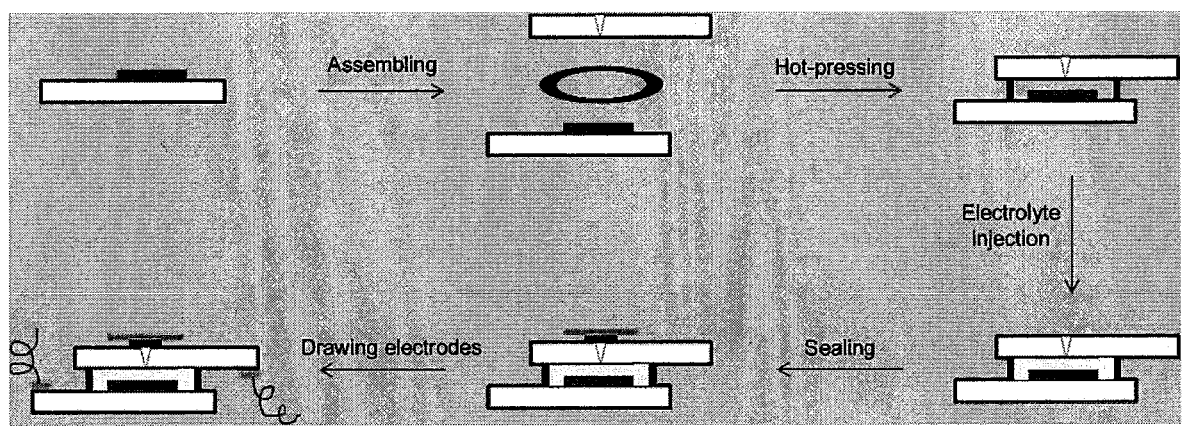

The schematic diagrams of the fabrication process and the structure of the dye-sensitized solar cell provided in Example 4 of the invention could be seen in FIG. 1 to FIG. 3, respectively. FIG. 1 is a schematic illustration of the device of the dye-sensitized solar cell provided by the invention; FIG. 2 is a schematic illustration of a light absorbing layer in the dye-sensitized solar cell provided by the invention; and FIG. 3 is a process flow chart of the manufacture of the dye-sensitized solar cell provided by the invention. As shown in FIG. 1, the dye sensitized solar cell according to the present invention, having a conventional construction, is consisted of two transparent substrate layers 1, a conductive layer 2, a light absorption layer 3, a hole transport layer 6 and the counter electrode 7. Inside the two transparent substrate layers 1, the conductive layer 2, the light absorption layer 3, the hole transport layer 6 and the counter electrode 7 are attached successively. As shown in FIG. 2, the light absorption layer 3 is consisted of a semitransparent micro/nanoparticle layer 4 and an organic dye layer 5, wherein the semitransparent micro/nanoparticle layer 4 is attached to the conductive layer 2, while the organic dye layer 5 is attached to the hole transport layer 6.

Under simulated AM1.5G sunlight (100 mW cm$^{-2}$), the prepared dye-sensitized solar cell was detected for the performance, and the test results were tabulated in Table 1. Table 1 was the results of performance tests of the dye-sensitized solar cells fabricated with the organic dyes provided in Examples of the invention.

TABLE 1

| Organic dye | Short-circuit current density [mA cm$^{-2}$] | Open-circuit voltage [mV] | Fill Factor | Cell efficiency [%] |
|---|---|---|---|---|
| Example 1 | 13.40 | 793 | 0.727 | 7.7 |
| Example 2 | 15.64 | 840 | 0.723 | 9.5 |
| Example 3 | 20.09 | 814 | 0.734 | 12.0 |

The description of the above Examples is only to help understanding the method of the present invention and the pivotal idea thereof. It should be understood that, for those skilled in the art, various improvements and modifications may also be made without departing from the principle of the invention. These improvements and modifications also fall in the protection scope of the claims of the invention.

What is claimed is:

1. An organic dye having a structure of formula (II);

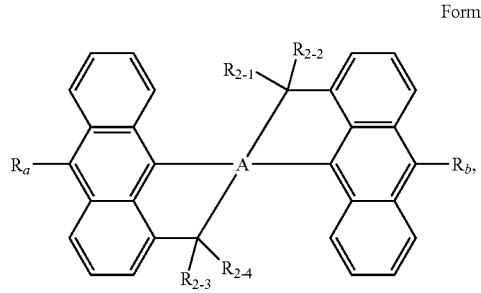

Formula (II)

wherein, $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

wherein $R_b$ is formula ($R_b$-1), formula ($R_b$-2), formula ($R_b$-3), or formula ($R_b$-4):

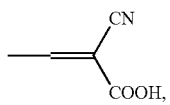

Formula ($R_b$-1)

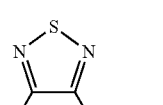

Formula ($R_b$-2)

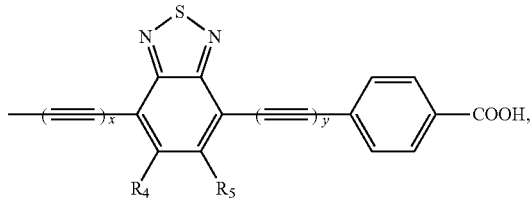

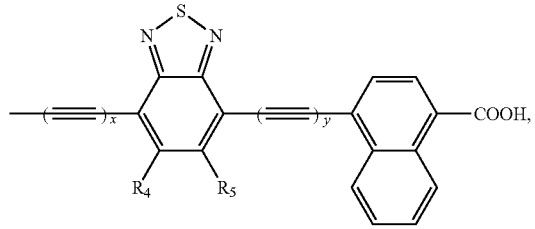

Formula ($R_b$-3)

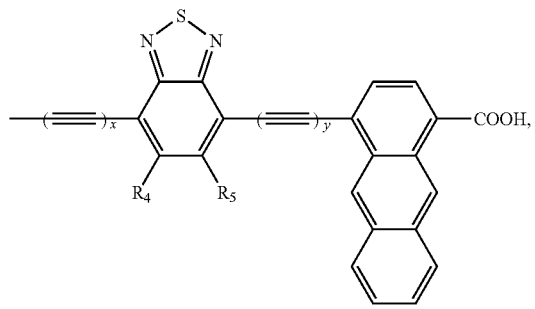

Formula ($R_b$-4)

wherein x and y are independently selected from 0 or 1, and both $R_4$ and $R_5$ are H;

wherein A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

wherein $R_{2-1}$, $R_{2-2}$, $R_{2-3}$, and $R_{2-4}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group.

2. An organic dye having a structure of formula (II);

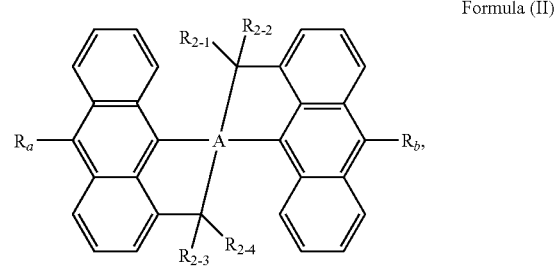

Formula (II)

wherein $R_a$ is formula ($R_a$-1), formula ($R_a$-2), formula ($R_a$-3), ($R_a$-4), formula ($R_a$-5), formula ($R_a$-6), or formula ($R_a$-7):

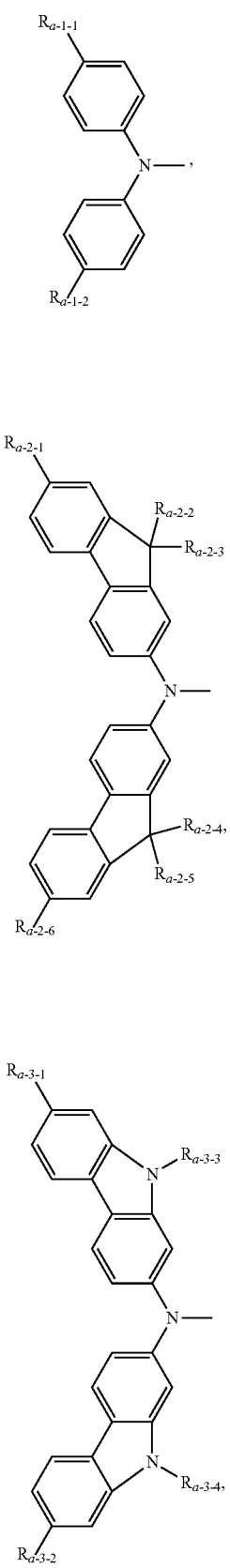
Formula (R$_a$-1)
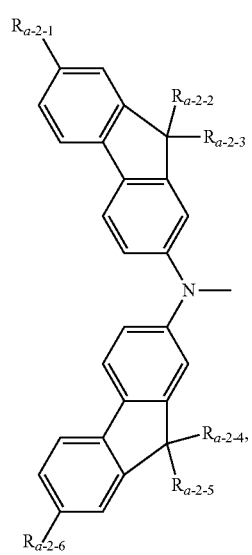
Formula (R$_a$-2)
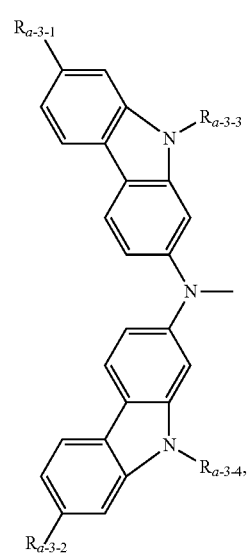
Formula (R$_a$-3)
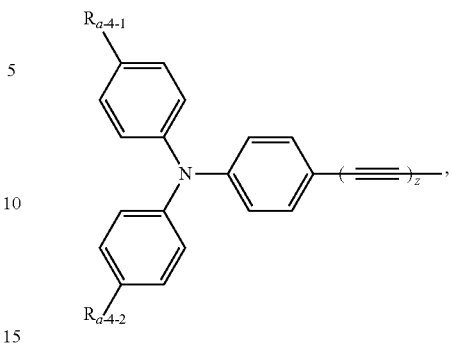
Formula (R$_a$-4)
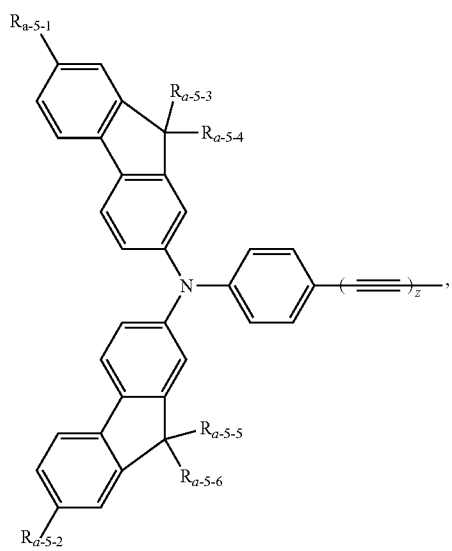
Formula (R$_a$-5)
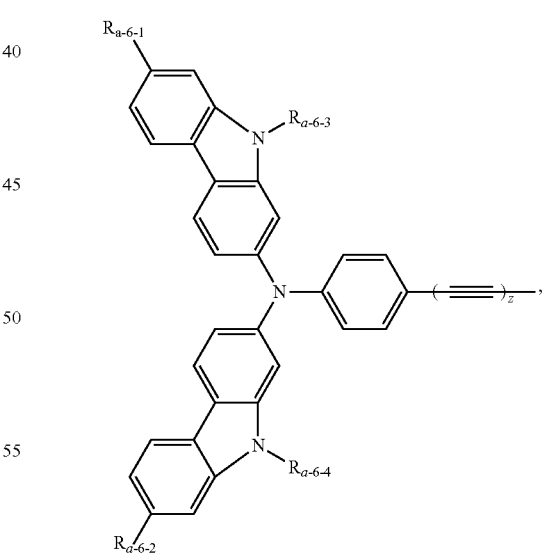
Formula (R$_a$-6)
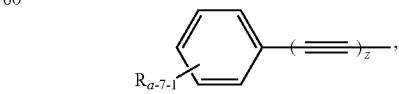
Formula (R$_a$-7)
wherein R$_{a\text{-}3\text{-}3}$, R$_{a\text{-}3\text{-}4}$, R$_{a\text{-}6\text{-}3}$, and R$_{a\text{-}6\text{-}4}$ are independently selected from H or a C$_1$-C$_{36}$ alkyl group;

wherein $R_{a\text{-}1\text{-}1}$, $R_{a\text{-}1\text{-}2}$, $R_{a\text{-}2\text{-}1}$, $R_{a\text{-}2\text{-}2}$, $R_{a\text{-}3\text{-}1}$, $R_{a\text{-}3\text{-}2}$, $R_{a\text{-}4\text{-}1}$, $R_{a\text{-}4\text{-}2}$, $R_{a\text{-}5\text{-}1}$, $R_{a\text{-}5\text{-}2}$, $R_{a\text{-}6\text{-}1}$, and $R_{a\text{-}6\text{-}2}$ are independently selected from H, a $C_1$-$C_{36}$ alkyl group, or a $C_1$-$C_{36}$ alkoxy group;

wherein $R_{a\text{-}2\text{-}3}$, $R_{a\text{-}2\text{-}4}$, $R_{a\text{-}2\text{-}5}$, $R_{a\text{-}2\text{-}6}$, $R_{a\text{-}5\text{-}3}$, $R_{a\text{-}5\text{-}4}$, $R_{a\text{-}5\text{-}5}$, and $R_{a\text{-}5\text{-}6}$ are independently selected from H, a $C_1$-$C_{36}$ alkyl group, a phenyl group substituted with a $C_1$-$C_{36}$ alkoxy group, or a phenyl group substituted with a $C_1$-$C_{36}$ alkyl group;

wherein $R_{a\text{-}7\text{-}1}$ is selected from H, a $C_1$-$C_{36}$ alkyl group, or a $C_1$-$C_{36}$ alkoxy group; and wherein z is 0 or 1;

wherein $R_b$ is formula ($R_b$-1), formula ($R_b$-2), formula ($R_b$-3), or formula ($R_b$-4):

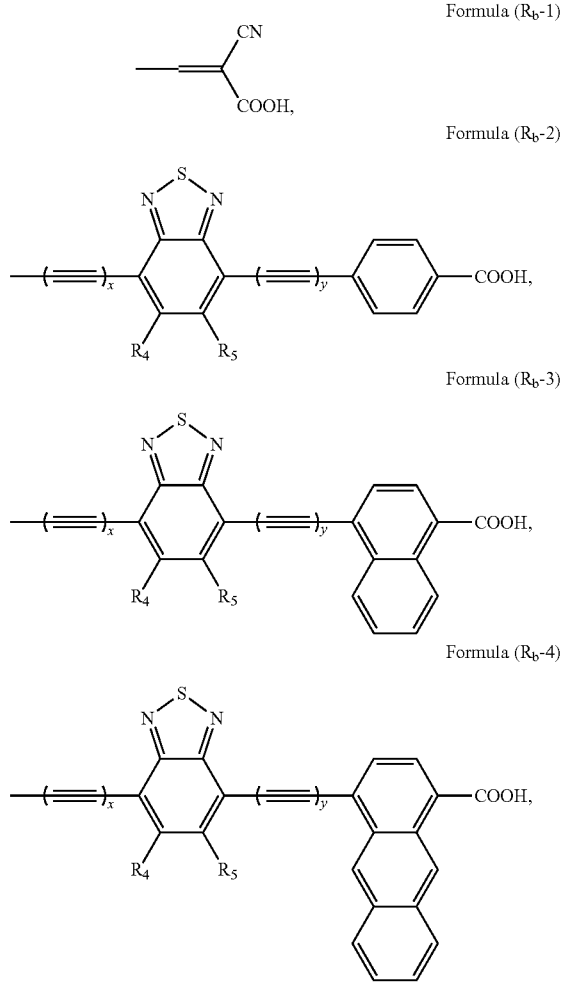

Formula ($R_b$-1)

Formula ($R_b$-2)

Formula ($R_b$-3)

Formula ($R_b$-4)

wherein x and y are independently selected from 0 or 1, and both $R_4$ and $R_5$ are H;

wherein A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

wherein $R_{2\text{-}1}$, $R_{2\text{-}2}$, $R_{2\text{-}3}$, and $R_{2\text{-}4}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group.

3. The organic dye according to claim 2, wherein $R_{a\text{-}3\text{-}3}$, $R_{a\text{-}3\text{-}4}$, $R_{a\text{-}6\text{-}3}$, and $R_{a\text{-}6\text{-}4}$ are independently selected from a $C_6$-$C_{30}$ alkyl group;

wherein $R_{a\text{-}1\text{-}1}$, $R_{a\text{-}1\text{-}2}$, $R_{a\text{-}2\text{-}1}$, $R_{a\text{-}2\text{-}2}$, $R_{a\text{-}3\text{-}1}$, $R_{a\text{-}3\text{-}2}$, $R_{a\text{-}4\text{-}1}$, $R_{a\text{-}4\text{-}2}$, $R_{a\text{-}5\text{-}1}$, $R_{a\text{-}5\text{-}2}$, $R_{a\text{-}6\text{-}1}$, and $R_{a\text{-}6\text{-}2}$ are independently selected from a $C_6$-$C_{30}$ alkyl group or a $C_6$-$C_{30}$ alkoxy group;

wherein $R_{a\text{-}2\text{-}3}$, $R_{a\text{-}2\text{-}4}$, $R_{a\text{-}2\text{-}5}$, $R_{a\text{-}2\text{-}6}$, $R_{a\text{-}5\text{-}3}$, $R_{a\text{-}5\text{-}4}$, $R_{a\text{-}5\text{-}5}$, and $R_{a\text{-}5\text{-}6}$ are independently selected from a $C_6$-$C_{30}$ alkyl group, a phenyl group substituted with a $C_6$-$C_{30}$ alkoxy group, or a phenyl group substituted with a $C_6$-$C_{30}$ alkyl group; and wherein $R_{a\text{-}7\text{-}1}$ is selected from a $C_6$-$C_{30}$ alkyl group or a $C_6$-$C_{30}$ alkoxy group.

4. The organic dye according to claim 1, wherein A is formula (A-1), formula (A-2), formula (A-3), formula (A-4), or formula (A-5):

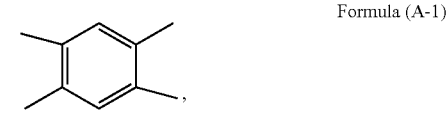

Formula (A-1)

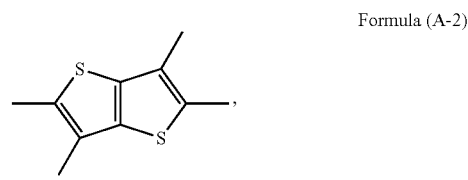

Formula (A-2)

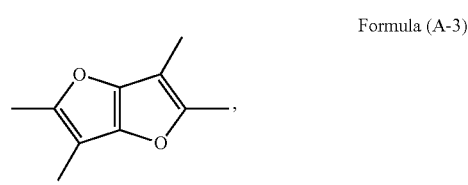

Formula (A-3)

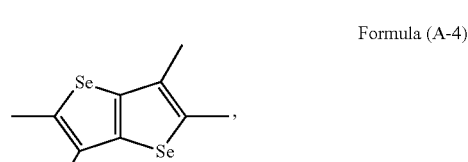

Formula (A-4)

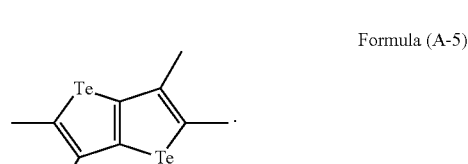

Formula (A-5)

5. The organic dye according to claim 1, wherein $R_{2\text{-}1}$, $R_{2\text{-}2}$, $R_{2\text{-}3}$, and $R_{2\text{-}4}$ are independently selected from a $C_6$-$C_{30}$ alkyl group, a phenyl group substituted with a $C_6$-$C_{30}$ alkyl group, or a phenyl group substituted with a $C_6$-$C_{30}$ alkoxy group.

6. The organic dye according to claim 1, wherein the organic dye has the structure of formula (II-1) or formula (II-2):

Formula (II-1)
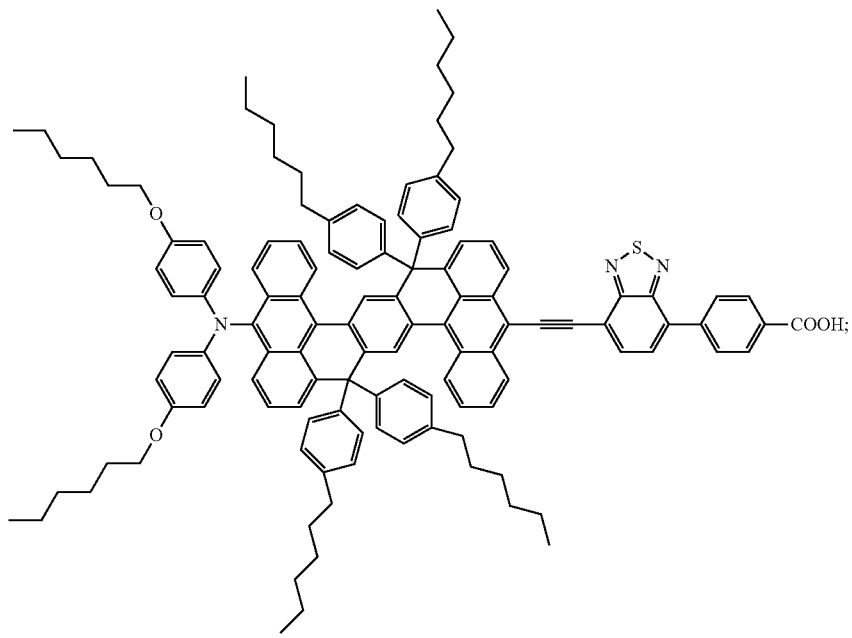
Formula (II-2)
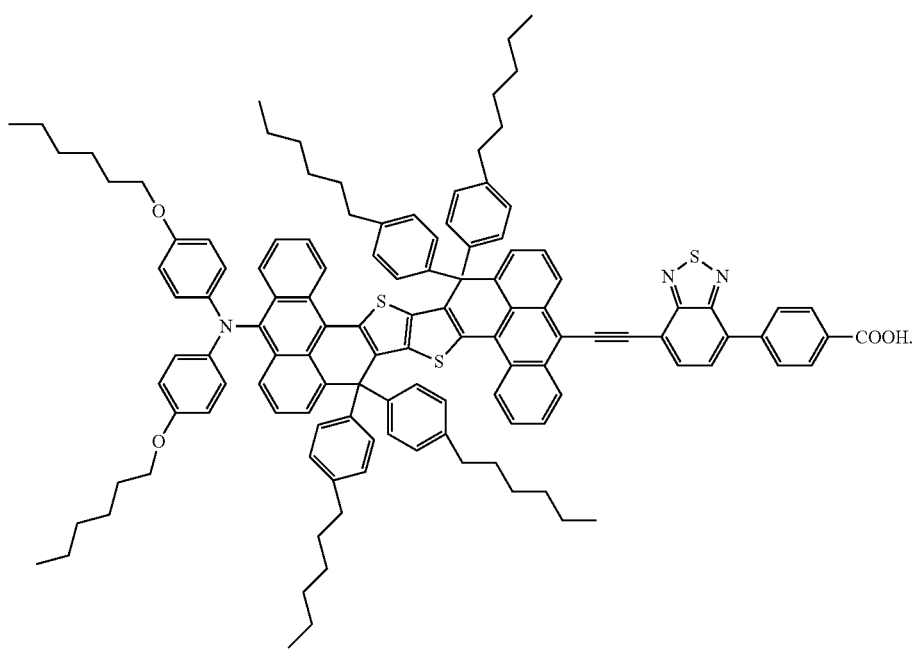
7. A preparation method for the organic dye of claim 1, comprising:
reacting a compound of formula (IV) with a compound of formula (V) to obtain the compound of formula (II);

Formula (IV)

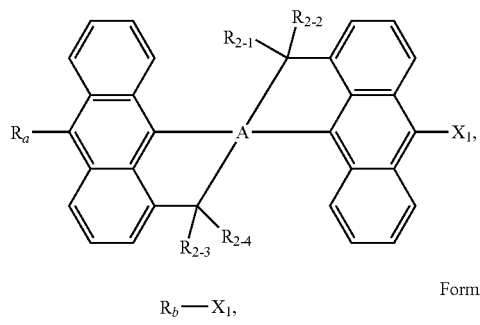

Formula (V)

$R_b$—$X_1$, wherein $R_a$ is H, an amino group substituted with a $C_6$-$C_{50}$ aryl group, an amino group substituted with a $C_6$-$C_{50}$ heteroaryl group, an unsaturated hydrocarbyl group substituted with a $C_6$-$C_{50}$ aryl group, an unsaturated hydrocarbyl group substituted with a $C_6$-$C_{50}$ heteroaryl group, a phenyl group substituted with a $C_1$-$C_{36}$ alkyl group, or a phenyl group substituted with a $C_1$-$C_{36}$ alkoxy group;

wherein A is a $C_6$-$C_{30}$ aryl group, a $C_4$-$C_{30}$ oxygen-containing heteroaryl group, a $C_4$-$C_{30}$ sulfur-containing heteroaryl group, a $C_4$-$C_{30}$ selenium-containing heteroaryl group, or a $C_4$-$C_{30}$ tellurium-containing heteroaryl group;

wherein $R_{2-1}$, $R_{2-2}$, $R_{2-3}$, and $R_{2-4}$ are independently selected from H, a $C_1$-$C_{36}$ alkyl group, a phenyl group substituted with a $C_1$-$C_{36}$ alkyl group, or a phenyl group substituted with a $C_1$-$C_{36}$ alkoxy group;

wherein $R_b$ is formula ($R_b$-1), formula ($R_b$-2), formula ($R_b$-3), or formula ($R_b$-4):

Formula ($R_b$-1)

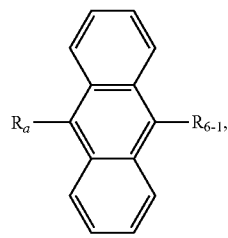

Formula ($R_b$-2)

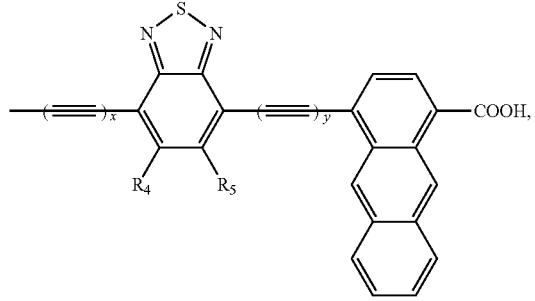

Formula ($R_b$-3)

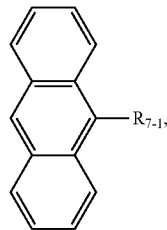

Formula ($R_b$-4)

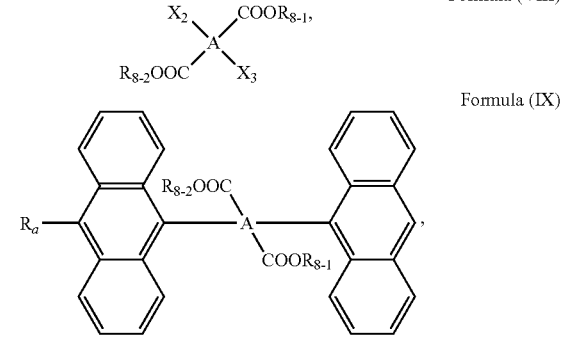

wherein x and y are independently selected from 0 or 1, and both $R_4$ and $R_5$ are H; and wherein $X_1$ is H, Br, or I.

8. The preparation method according to claim 7, wherein the compound of formula (IV) is prepared according to the following method,
1) mixing and reacting a compound of formula (VI), a compound of formula (VII), and a compound of formula (VIII) to obtain a compound of formula (IX);

Formula (VI)

Formula (VII)

Formula (VIII)

Formula (IX)

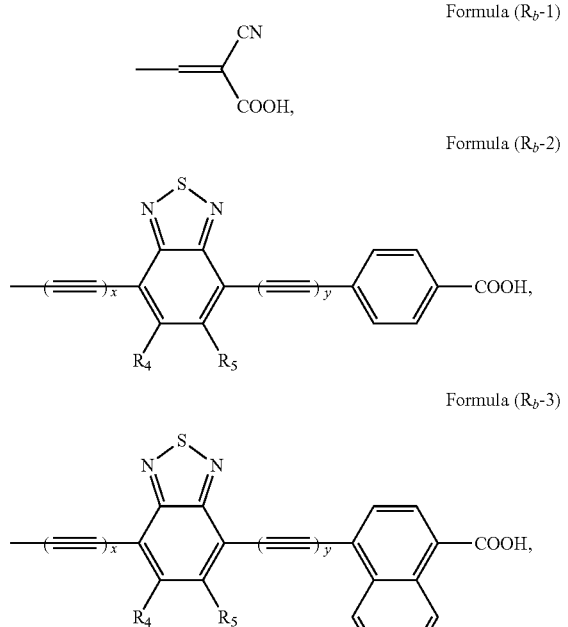

wherein $R_{6-1}$ and $R_{7-1}$ are independently selected from $(CH_3)_3Sn$—, $(n\text{-}Bu)_3Sn$—, or a borate ester group, wherein $R_{8-1}$ and $R_{8-2}$ are independently selected from a $C_1$-$C_8$ alkyl group, and wherein $X_2$ and $X_3$ are independently selected from Cl, Br, or I;

2) converting the compound of formula (IX) to the compound of formula (IV).

9. The preparation method according to claim 8, wherein the step 2) comprises:
2-1) converting the compound of formula (IX) to a compound of formula (X):

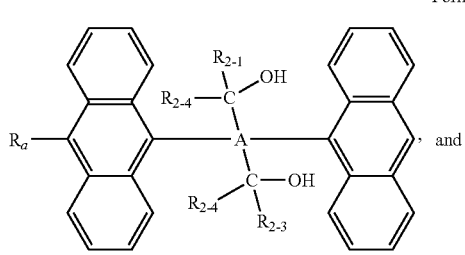

Formula (X)

2-2) converting the compound of formula (X) to a compound of formula (IV).

10. The preparation method according to claim 9, wherein a catalyst is used in the step 2-2) and said catalyst is a polymer resin with macroporous and strongly acidic properties.

11. The organic dye according to claim 2, wherein A is formula (A-1), formula (A-2), formula (A-3), formula (A-4), or formula (A-5):

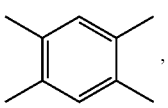

Formula (A-1)

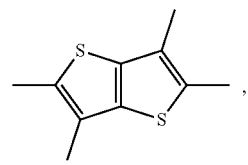

Formula (A-2)

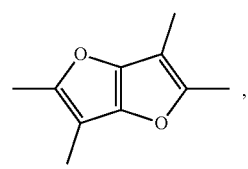

Formula (A-3)

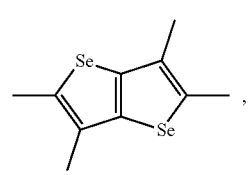

Formula (A-4)

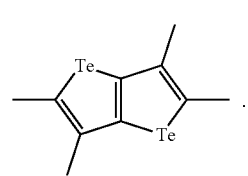

Formula (A-5)

12. The organic dye according to claim 2, wherein $R_{2-1}$, $R_{2-2}$, $R_{2-3}$, and $R_{2-4}$ are independently selected from a $C_6$-$C_{30}$ alkyl group, a phenyl group substituted with a $C_6$-$C_{30}$ alkyl group, or a phenyl group substituted with a $C_6$-$C_{30}$ alkoxy group.

* * * * *

UNITED STATES PATENT AND TRADEMARK OFFICE
CERTIFICATE OF CORRECTION

PATENT NO. : 10,563,064 B2
APPLICATION NO. : 16/088710
DATED : February 18, 2020
INVENTOR(S) : Wang et al.

Page 1 of 1

It is certified that error appears in the above-identified patent and that said Letters Patent is hereby corrected as shown below:

In the Specification

Column 12, Line 34, Formula X: Please correct "$R_{2\text{-}4}$" to read -- $R_{2\text{-}2}$ --

Column 17, Line 4: Please correct "$R_{a\text{-}2}$" to read -- $R_{a\text{-}2\text{-}4}$, --

Column 17, Line 43: Please correct "R" to read -- $R_{a\text{-}6\text{-}1}$ --

Column 24, Line 22: Please correct "$R_{24}$" to read -- $R_{2\text{-}4}$ --

Signed and Sealed this
Seventh Day of July, 2020

Andrei Iancu
*Director of the United States Patent and Trademark Office*